(12) United States Patent
Kataoka et al.

(10) Patent No.: US 7,461,551 B2
(45) Date of Patent: Dec. 9, 2008

(54) WINDOW FOG DETECTING APPARATUS

(75) Inventors: Takuya Kataoka, Okazaki (JP); Teruo Oda, Gamagori (JP)

(73) Assignee: Denso Corporation, Kariya (JP)

( * ) Notice: Subject to any disclaimer, the term of this patent is extended or adjusted under 35 U.S.C. 154(b) by 378 days.

(21) Appl. No.: 11/377,494

(22) Filed: Mar. 16, 2006

(65) Prior Publication Data

US 2006/0207325 A1 Sep. 21, 2006

(30) Foreign Application Priority Data

Mar. 17, 2005 (JP) ............................. 2005-077279
Nov. 29, 2005 (JP) ............................. 2005-343659

(51) Int. Cl.
*G01N 21/81* (2006.01)
(52) U.S. Cl. ................. 73/335.01; 250/208.1
(58) Field of Classification Search ............. 73/335.01, 73/1.45, 1.88; 250/208.1
See application file for complete search history.

(56) References Cited

U.S. PATENT DOCUMENTS

| | | | |
|---|---|---|---|
| 5,923,027 A | | 7/1999 | Stam et al. |
| 6,097,024 A | | 8/2000 | Stam et al. |
| 6,681,163 B2 | * | 1/2004 | Stam et al. ..................... 701/36 |
| 6,853,897 B2 | * | 2/2005 | Stam et al. ..................... 701/36 |
| 7,019,275 B2 | * | 3/2006 | Stam et al. ............... 250/208.1 |
| 7,199,346 B2 | * | 4/2007 | Stam et al. ............... 250/208.1 |
| 2008/0121034 A1 | * | 5/2008 | Lynam et al. ............ 73/335.05 |

FOREIGN PATENT DOCUMENTS

| | | |
|---|---|---|
| JP | 59-108939 | 6/1984 |
| JP | 5-294139 | 11/1993 |
| JP | 2000-296762 | 10/2000 |

* cited by examiner

*Primary Examiner*—Hezron Williams
*Assistant Examiner*—Rodney T Frank
(74) *Attorney, Agent, or Firm*—Harness, Dickey & Pierce, PLC

(57) ABSTRACT

A window fog detecting apparatus has an optical type fog detecting sensor for optically detecting fog occurring at a window glass, a humidity sensor for detecting a relative humidity of air at an interior side of the window glass, and a sensor output correcting unit. When a fog occurrence at the window glass is determined based on the output values of the optical type fog detecting sensor, the sensor output correcting unit corrects the relative humidity detected by the humidity sensor based on output values of the optical type fog detecting sensor.

18 Claims, 11 Drawing Sheets

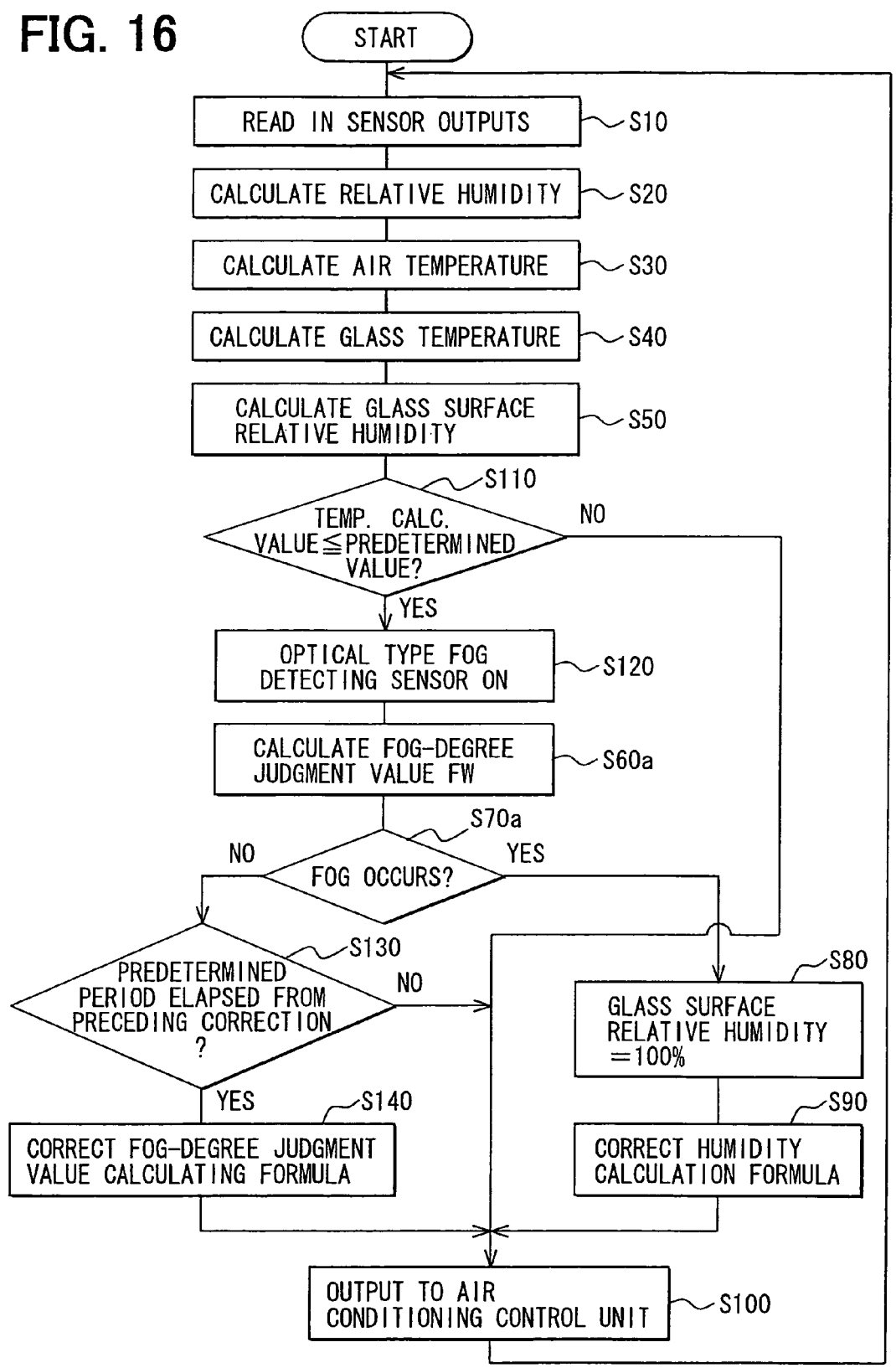

WINDOW FOG DETECTING APPARATUS

CROSS REFERENCE TO RELATED APPLICATION

This application is based on Japanese Patent Applications No. 2005-77279 filed on Mar. 17, 2005 and No. 2005-343659 filed on Nov. 29, 2005, the disclosure of which is incorporated herein by reference.

FIELD OF THE INVENTION

The present invention is related to a window fog detecting apparatus, which is suitably used for a vehicle, for example.

BACKGROUND OF THE INVENTION

Generally, window fog detecting apparatuses for vehicles are mainly classified into a humidity detection type and an optical type. The window fog detecting apparatus of the humidity detection type judges whether or not fog occurs at a window glass of the vehicle by comparing a glass temperature with a dew-point temperature of ambient air thereof. In this case, the dew-point temperature is calculated based on outputs of a humidity sensor and an air temperature sensor, which are arranged in a passenger compartment of the vehicle.

The glass temperature can be detected through a temperature sensor (i.e., contact detection means) mounted at an inner surface of the window glass, or an infrared sensor (i.e., non-contact detection means), or the like. Alternatively, the glass temperature can be also calculated (i.e., estimation means) according to, for example, a vehicle exterior temperature, a vehicle speed and a vehicle interior temperature.

In the window fog detecting apparatus of the humidity detection type, a relative humidity of interior air is converted into a relative humidity (glass surface relative humidity) at the glass temperature so as to judge a fog occurrence at the window glass, without comparing the glass temperature with the dew-point temperature.

The window fog detecting apparatus of the optical type detects the fog occurrence at the inner surface of the window glass by using an optical sensor in a non-contact means. For example, referring to JP-59-108939-A, a light receiving unit and a light emitting unit are provided to detect a reduction of direct reflection light due to a fog occurrence at the window glass. Referring to JP-2000-296762-A and JP-5-294139-A, the fog occurrence at the window glass is detected by sensing an increase of scattered reflection light due to fog at the window glass. Furthermore, referring to U.S. Pat. No. 6,097,024 (JP-2004-212404-A), the window fog detecting apparatus of the optical type judges the fog occurrence at the window glass by an image processing operation.

In these cases, a dehumidifying operation (operation of compressor) of a refrigerant cycle for an air conditioner of the vehicle is restricted in such a range that fog does not occur at the window glass. Therefore, the operating ratio of the dehumidifying operation is reduced so as to lower the compressor power. Thus, the fuel consumption of a vehicle engine which drives the compressor is decreased. Moreover, the vehicle is provided with the window fog judging operation and a control for heightening the window fog-preventing performance of the air conditioner, in order to prevent fog from occurring at the window glass.

Furthermore, at a low temperature in winter or the like, the inside air ratio of suction air in the air conditioner is increased within such a range that fog does not occur at the window glass. Thus, the ventilation heat loss is reduced and the heating performance of the air conditioner is improved.

However, in the window fog detecting apparatus of the humidity detection type, because there exist the detection accuracy variation and the durability deterioration of the humidity sensor, a large safety rate must be set with respect to the output value of the humidity sensor for the window fog judging operation in order to control to prevent fog from occurring at the window glass. Therefore, the above-described reduction effects of the compressor power and the ventilation heat loss cannot be sufficiently achieved.

Moreover, the window fog detecting apparatus of the optical type can only detect fog occurring at the part of the window glass where the sensor is mounted, although the window fog detecting apparatus of the optical type has a detection accuracy higher than that of the humidity detection type. Thus, fog may occur at other part of the window glass where the sensor is not arranged. Because the position where fog starts differs in response to vehicles, it is cumbersome to determine the sensor installation portions when the vehicles are developed.

SUMMARY OF THE INVENTION

In view of the above-described disadvantages, it is an object of the present invention to provide a window fog detecting apparatus, in which a humidity detection has a high accuracy over a long period.

It is another object of the present invention to provide a window fog detecting apparatus, in which a fog detection has a high accuracy over a long period.

According to an aspect of the present invention, a window fog detecting apparatus is provided with an optical type fog detecting sensor for optically detecting fog occurring at a window glass, a humidity sensor for detecting a relative humidity of air at an interior side of the window glass for the sake of an anti-fog control which is performed to prevent fog from occurring at the window glass, and a sensor output correcting unit. When a fog occurrence at the window glass is determined based on the output values of the optical type fog detecting sensor, the sensor output correcting unit corrects the relative humidity detected by the humidity sensor based on output values of the optical type fog detecting sensor in the case where there exits a difference about the fog occurrence at the window glass between the relative humidity detected by the humidity sensor and the output values of the optical type fog detecting sensor.

Because the surface relative humidity of the window glass becomes 100% when fog occurs thereat, the fog occurrence at the window glass can be substantially detected based on the output values of the optical type fog detecting sensor. According to the present invention, the detection deviation, the durability deterioration and the like of the humidity sensor can be self-corrected by the sensor output correcting unit, with the criterion of the surface relative humidity of 100%. Therefore, the humidity detection can be provided with a high accuracy over a long period. Moreover, in this case, the fog occurrence can be appropriately detected over the whole window glass.

According to another aspect of the present invention, a window fog detecting apparatus has an optical type fog detecting sensor which includes a light emitting unit for emitting light toward a window glass and a light receiving unit for receiving reflection light from the window glass, a fog-degree calculating unit for calculating a fog-degree judgment value based on a ratio of projection light from the light emitting unit to the reflection light, a fog judging unit for judging a fog occurrence at the window glass based on the fog-degree judgment value, and a first correction unit. The first correction unit corrects a calculation formula of the fog-degree judgment value, so that the fog-degree judgment value becomes substantially equal to a value indicating a non-occurrence of fog at the window glass in the case where the non-occurrence of fog at the window glass is determined by the fog judging unit.

Therefore, the fog-degree judgment value can be normalized, so that the deterioration of the fog-degree judging accuracy due to the durability deterioration and the like of the light emitting unit 15 and the contamination of the window glass 12 can be restricted. Thus, the decrease of projection light due to the durability deterioration and the like of the light emitting unit 15 and the decrease of reflection light due to the contamination of the window glass 12 can be restricted, so that the optical-typed fog detection accuracy can be improved over a long period.

BRIEF DESCRIPTION OF THE DRAWINGS

Other objects, features and advantages of the present invention will become more apparent from the following detailed description made with reference to the accompanying drawings, in which:

FIG. 16 is a flow chart showing a window fog detection operation according to the ninth embodiment.

DETAILED DESCRIPTION OF THE PREFERRED EMBODIMENTS

First Embodiment

A window fog detecting apparatus 10 according to a first embodiment of the present invention will be described with reference to FIGS. 1-14. The window fog detecting apparatus 10 can be suitably used for an air conditioner for a vehicle, for example.

Figure 1:
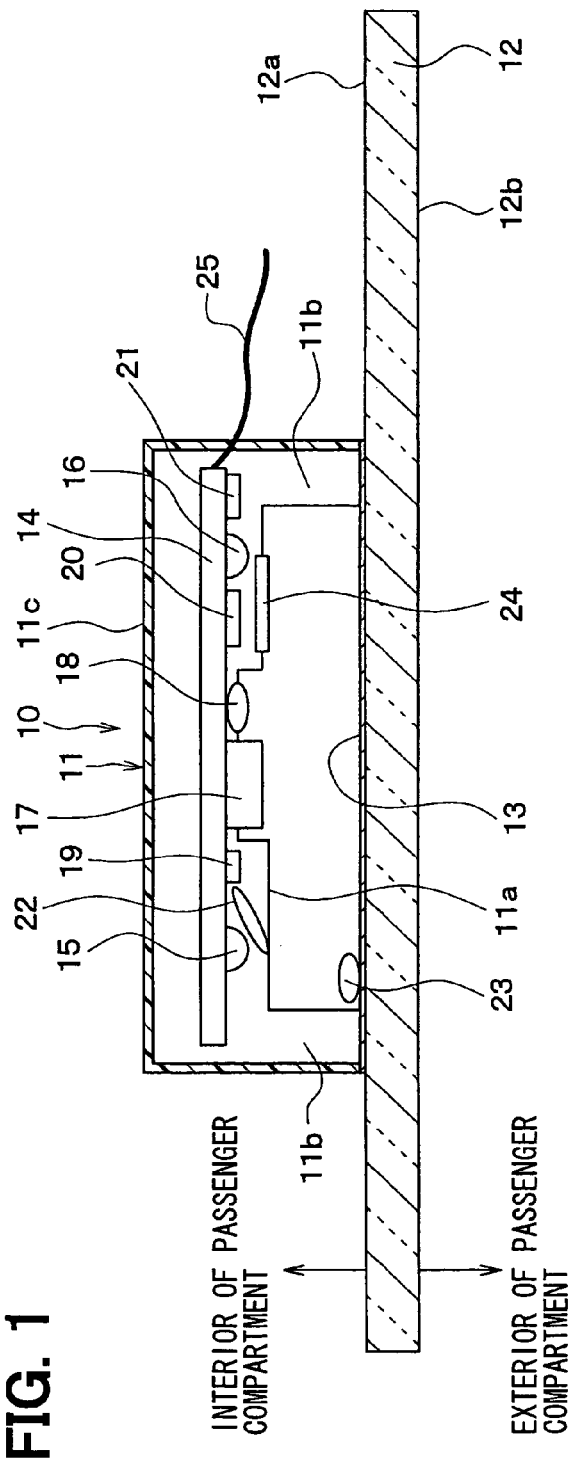
FIG. 1 is a schematic cross-sectional view showing a window fog detecting apparatus according to a first embodiment of the present invention.
Figure 2:
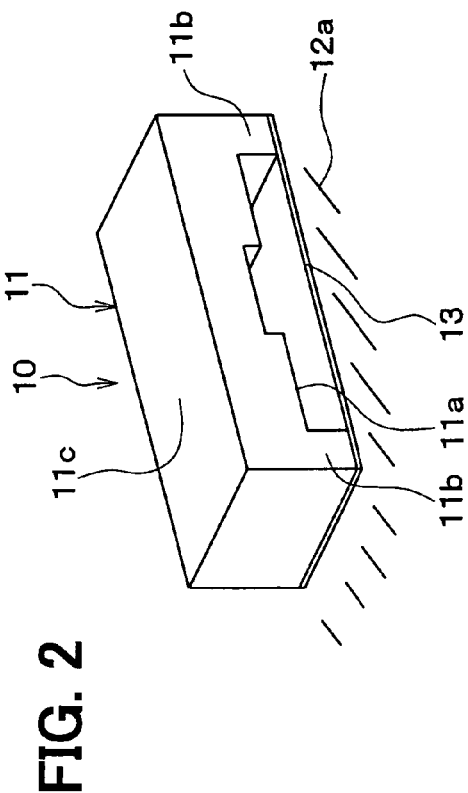
FIG. 2 is a schematic perspective view showing the window fog detecting apparatus according to the first embodiment.

As shown in FIGS. 1 and 2, the window fog detecting apparatus 10 is provided with a case unit 11 made of a resin, for example. The case unit 11 has a substantially rectangular parallelepiped shape with a small height. The case unit 11 has a substantially convex-shaped opening portion 11a which is opened at a front wall portion and a back wall portion of the case unit 11. The lower portion (bottom portion) of the case unit 11 is completely opened.

The interior space of the case unit 11 is currently communicated with a peripheral space (e.g., interior of passenger compartment of vehicle) of the case unit 11 through the opening portion 11a which penetrates the front wall portion and the back wall portion of the case unit 11.

Referring to FIG. 1, a right wall portion and a left wall portion (respectively at right side and left side of opening portion 11a) of the case unit 11 function as mounting stay portions 11b when being attached to an inner surface 12a of a window glass 12 (e.g., windshield of vehicle) which is arranged between an interior space and an exterior space.

The inner surface 12a (positioned at upper side of FIG. 1) faces the interior of the passenger compartment, and an outer surface 12b (positioned at lower side of FIG. 1) of the window glass 12 faces the exterior of the passenger compartment.

A lightproof film 13 having a thin film-shaped is fixed (e.g., by adhering) to lower end surfaces of the mounting stay portions 11b and the inner surface 12a (of window glass 12) within the range of the bottom portion of the case unit 11. The lightproof film 13 is made of a light-proof material having a high thermal conductivity, for example, a metal such as aluminum, to restrict light from entering the interior of the case unit 11 through the window glass 12. That is, the lightproof film 13 has a high (superior) thermal conductivity and a high (superior) light reflectivity. Therefore, the temperature of the lightproof film 13 can become substantially same with that of the inner surface 12a of the window glass 12, so that the fog occurrence at the surface of the lightproof film 13 has a substantially same temperature condition with that of the window glass 12. In this case, scattered light from the exterior passing through the window glass 12 can be isolated from entering the light receiving unit, thus improving the detection accuracy of the fog occurrence.

A circuit board 14 is arranged in the internal space of the case unit 11, and disposed between an upper end of the opening portion 11a and an upper wall portion 11c of the case unit 11. The circuit board 14 is arranged substantially parallel to the window glass 12, and fixed to an inner surface of the case unit 11. The circuit board 14 is, for example, a printed circuit board which constructs a conductor circuit portion at an insulating board.

Referring to FIGS. 1 and 2, a light emitting unit 15, a light receiving unit 16, a humidity sensor 17, a temperature sensor 18 for detecting an air temperature, an amplifier unit 19, a calculation circuit 20, and a communication circuit 21 are mounted on a lower surface (at side of window glass 12) of the circuit board 14. An optical-typed fog detecting sensor is constructed of the light emitting unit 15 and the light receiving unit 16.

The humidity sensor 17 and the temperature sensor 18 are arranged at a substantial longitudinal-direction center portion of the circuit board 14, and positioned near the upper end of the opening portion 11a. That is, the humidity sensor 17 and the temperature sensor 18 are positioned to be communicated with the interior of the passenger compartment of the vehicle. Thus, the humidity sensor 17 and the temperature sensor 18 can representatively detect a humidity and a temperature of air near the inner surface 12a of the window glass 12 in the vehicle. The longitudinal direction of the circuit board 14 corresponds the right-left direction of FIGS. 1 and 2.

A temperature sensor 23 for detecting a glass temperature of the window glass 12 is integrated with the lightproof film 13, and disposed at a surface thereof of the side of the case unit 11. As described above, because the lightproof film 13 is made of the thin film-shaped material having the high thermal conductivity, the temperature of the lightproof film 13 can become substantially equal to the temperature of the inner surface 12a (at inner side of passenger compartment) of the window glass 12.

In this case, the humidity sensor 17 can be a capacitance variation type, where a dielectric constant of a humidity sensitive film varies in response to a relative humidity of air so that a capacitance thereof varies in response to the relative humidity of air.

Each of the temperature sensors 18 and 23 is constructed of a thermistor which has a resistance value varies in response to a temperature. The light emitting unit 15 is constructed of a light emitting diode, and the light receiving unit 16 is constructed of a photodiode where output current varies in response to a light receiving amount thereof.

The photodiode of the light receiving unit 16 has a characteristic that the output current thereof increases in response to an increase of the light receiving amount thereof. When fog occurs at the window glass 12, (specifically, on lightproof film 13), light is scattered due to water droplets of fog so that light reflected toward the photodiode is decreased. Thus, the light receiving amount of the photodiode is decreased, so that the output current of the photodiode is reduced.

A lens 22 is arranged at a light exit side of the light emitting unit 15. When light emitted from the light emitting unit 15 is reflected on the surface of the lightproof film 13 to reach the light receiving unit 16, the reflection light can be focused at the light receiving unit 16 through the lens 22.

A filter 24 is arranged at a light entrance side of the light receiving unit 16. The filter 24 is set so that only light having a wavelength range near that of the light emitted by the light emitting unit 15 can penetrate the filter 24.

Referring to FIG. 1, the upper surface (of side of case unit 11) of the lightproof film 13 is glossy so as to increase a reflectance of the lightproof film 13. Thus, there occurs a large difference between the amounts of light reflected toward the light receiving unit 16 in the case of a fog occurrence on the surface of the lightproof film 13 and in the case of no-fog occurrence thereon. Therefore, window fog can be easily detected.

A lead wire 25 is constructed of a power supply line and a communication line, which extends from the internal space of the case unit 11 to the external thereof. The lead wire 25 is used to electrically connect an electric circuit unit (amplifier unit 19, calculation circuit 20, and communication circuit 21) of the circuit board 14 to an external circuit (air conditioning control unit 26, vehicle power supply and the like shown in FIG. 4).

The interval between the inner surface 12a of the window glass 12 and each of the circuit board 14 and the various sensors mounted on the circuit board 14 is defined by the mounting stay portion 11b of the case unit 11.

Next, the constitution of an electrical control system of the window fog detecting apparatus 10 will be described with reference to FIG. 3.

Output signals from the light receiving unit 16 and the sensors 17, 18, and 23 are respectively amplified by amplifiers 19a, 19b, 19c and 19d of the amplifier unit 19, and then respectively sent to calculation circuits 20a, 20b, 20c and 20d.

A calculation formula correcting circuit 20e (sensor output correcting unit) and a glass surface relative humidity calculation circuit 20f are provided. The calculation formula correcting circuit 20e corrects a humidity calculation formula based on a calculated value of a fog judgment calculation circuit 20a. The glass surface relative humidity calculation circuit 20f calculates a glass surface relative humidity (relative humidity of inner surface 12a of window glass 12) based on a calculated value of a relative humidity calculation circuit 20b, a calculated value of an air temperature calculation circuit 20c, and a calculated value of a glass temperature calculation circuit 20d. Calculated values of the calculation circuits 20f and 20a are sent to the air conditioning control unit 26 via a communication circuit 21.

Figure 4:
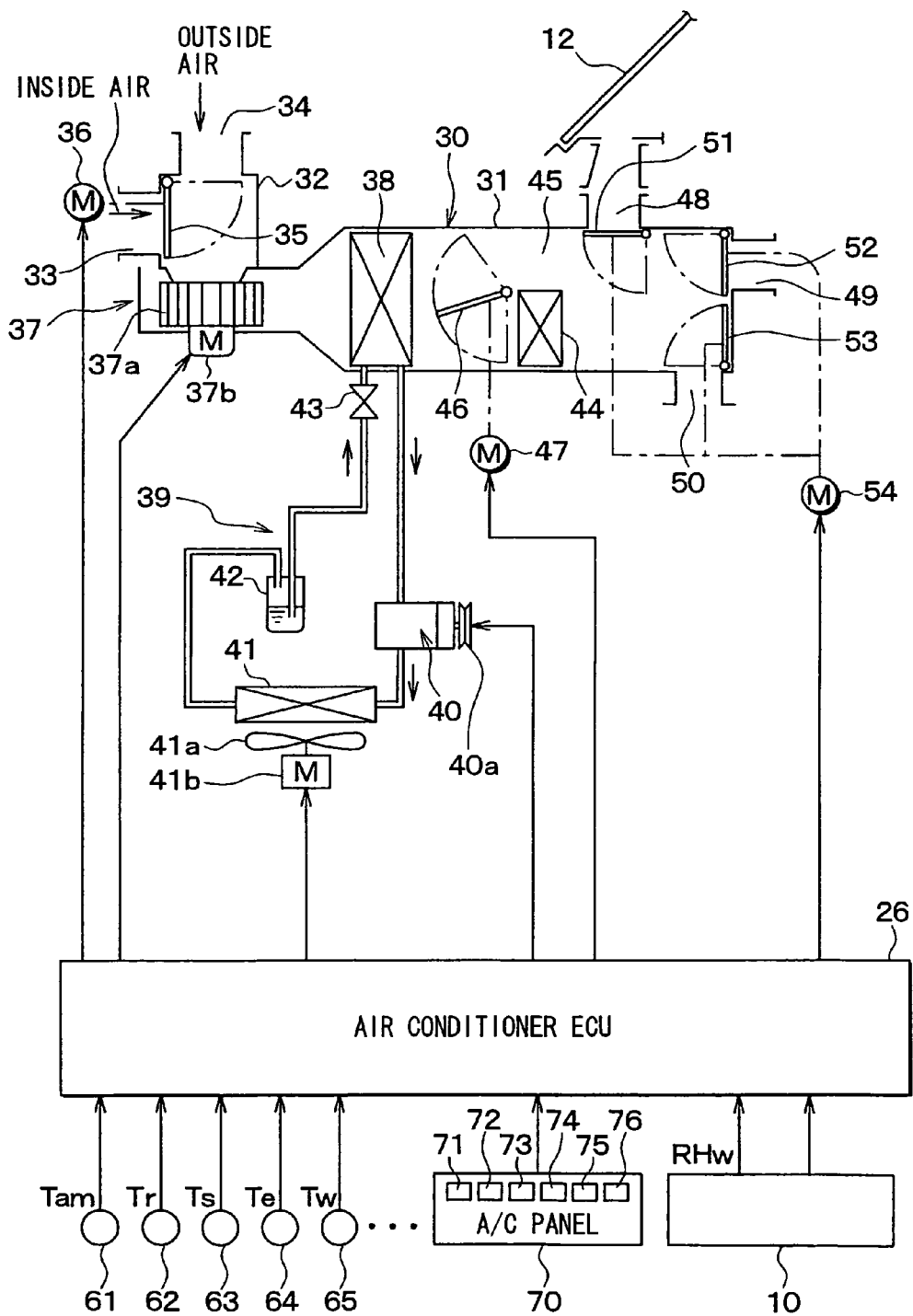
FIG. 4 is a schematic view showing a whole construction of an air conditioner for a vehicle according to the first embodiment.

Next, the whole construction of the air conditioner for the vehicle will be described with reference to FIG. 4.

The air conditioner is provided with an interior air conditioning unit 30 which is arranged at, for example, an inside portion of an instrument panel located at a frontmost portion of the passenger compartment. The interior air conditioning unit 30 has a case unit 31 defining therein an air passage, through which air is blown toward the interior of the passenger compartment.

An inside/outside air switching box 32 is arranged at the most upstream side of the air passage in the case unit 31. An inside air introduction port 33 and an outside air introduction port 34 are formed at the inside/outside air switching box 32, and selectively opened/closed by an inside/outside air switching door 35 (inside/outside air switching unit) which is driven by a servo motor 36 or the like.

A blower 37 of, for example, a motor-driven type, is arranged on the air downstream side of the inside/outside air switching box 32, to blow air toward the interior of the passenger compartment. The blower 37 has a blowing fan 37a (of centrifugal type, for example) and a motor 37b for driving the blowing fan 37a.

An evaporator 38, being a cooling heat exchanger for cooling blown air, is arranged at the air downstream side of the blower 37. In the evaporator 38 which is a part of a refrigerant cycle system 39 of the air conditioner, low-temperature low-pressure refrigerant absorbs heat from blown air to be evaporated so that blown air is cooled.

The refrigerant cycle system 39 further has a compressor 40, a condenser 41, a fluid receiver 42, an expansion valve 43 and the like. Refrigerant is circulated from an air exhaust side of the compressor 40 via the condenser 41, the fluid receiver 42, and the expansion valve 43 (which is decompression unit) to the evaporator 38. Air (cool air) outside the passenger compartment is blown to the condenser 41 by a motor-driven type cooling fan 41a, for example. The cooling fan 41a can be driven by a motor 41b.

In the refrigerant cycle system 39, the compressor 40 can be driven by a vehicle engine (not shown) via an electromagnetic clutch 40a. Thus, the operation of the compressor 40 can be intermittently controlled by intermittently power-supplying the electromagnetic clutch 40a.

On the other hand, a heater core 44 is provided at the downstream side of the evaporator 38 in the interior air conditioning unit 30, to heat air which flows through the air passage of the case unit 31. The heater core 44 is a heating heat exchanger in which warm water (i.e., engine cooling water) of the vehicle engine is used as a heat source for heating air (cool air) having passed through the evaporator 38. A bypass passage 45 is arranged at a side of the heater core 44 so that air flows through the bypass passage 45 to bypass the heater core 44.

An air mixing door 46 (temperature adjusting unit) is rotatably arranged between the evaporator 38 and the heater core 44. The air mixing door 46 is driven by a servo motor 47 or the like so that a rotation position (open degree) of the air mixing door 46 can be continuously adjusted.

A ratio of an amount of air (warm air amount) flowing through the heater core 44 to an amount of air (cool air amount) which flows through the bypass passage 45 to bypass the heater core 44 is adjusted based on the open degree of the air mixing door 46. Thus, a temperature of air blown into the passenger compartment can be adjusted via the air mixing door 46.

A defroster blowing-out port 48, a face blowing-out port 49, a foot blowing-out port 50 and the like are arranged at the most downstream side of the air passage of the case unit 31. Conditioned air can be adjusted and blown toward the window glass 12 of the vehicle through the defroster blowing-out port 48, toward a face portion of a passenger through the face blowing-out port 49, toward a foot portion of the passenger through the food blowing-out port 50, and the like.

A defroster door 51, a face door 52, a foot door 53 and the like are respectively rotatably arranged at the air upstream sides of the blowing-out ports 48-50. The doors 51-53 are selectively opened/closed by a servo motor 54 or the like via a link mechanism (not shown).

The air conditioning control unit 26 is constructed of a well-known microcomputer and a peripheral circuit thereof. The microcomputer has a CPU, a ROM, a RAM and the like. A control program for an air conditioning control operation is beforehand memorized in the ROM, and the air conditioning control unit 26 executes various calculations and process operations based on the memorized control program.

The calculation value of the window fog detecting apparatus 10, detection signals from well-known air conditioner sensors 61-65 and operation signals from an air conditioning operation panel 70 are inputted to the air conditioning control unit 26.

Specifically, the outside air sensor 61 detects an outside air temperature (temperature of air outside passenger compartment) Tam. The inside air sensor 62 detects an inside air temperature (temperature of air inside passenger compartment) Tr. The solar radiation sensor 63 detects a solar radiation amount Ts entering the passenger compartment. The evaporator temperature sensor 64 is arranged at an air blowing-out portion of the evaporator 38 to detect an evaporator blowing-out air temperature Te. The water temperature sensor 65 detects a temperature Tw of warm water (engine cooling water) which flows into the heater core 44.

The air conditioning operation panel 70 is provided thereon with various air conditioner operating members, for example, a temperature setting switch 71, a blowing-out mode switch 72, an inside/outside air selecting switch 73, an air conditioning switch 74, a blower actuation switch 75, an automatic switch 76 and the like.

The temperature setting switch 71 is a temperature setting unit through which the temperature in the passenger compartment is set. The blowing-out mode switch 72 is provided to manually set blowing-out modes which are selectively switched through the blowing-out mode doors 51-53. The inside/outside air selecting switch 73 is provided to manually set inside/outside air suction modes through the inside/outside air switching door 35. The air conditioning switch 74 is provided to output an actuation command signal (that is, ON signal of electromagnetic clutch 40a) of the compressor 40. The blower actuation switch 75 is provided to manually set an air-blowing amount of the blower 37. The automatic switch 76 is provided to output a command signal of an air-conditioner automatic control state.

The electromagnetic clutch 40a of the compressor 40, the servo motors 36, 47, 54 (electrical driving units of above-described devices), the motor 37b of the blower 37, the motor 41b of the condenser cooling fan 41a and the like are connected to the output side of the air conditioning control unit 26 to be controlled based on output signals of the air conditioning control unit 26.

Next, the operation of the air conditioner according to the first embodiment will now be described.

At first, the operation of the interior air conditioning unit 30 is described. When the blower 37 is actuated, air which is introduced from the inside air introduction port 33 and/or the outside introduction port 34 is blown toward the vehicle interior through the interior of the case unit 31. Moreover, the electromagnetic clutch 40a is energized to become a connection state. The compressor 40 is driven by the vehicle engine, so that refrigerant is circulated in the refrigerant cycle system 39.

Blown air of the blower 37 firstly passes the evaporator 38 to be cooled and dehumidified. Then, cool air is divided into an air flow which will pass the heater core 44 and an air flow which will pass the bypass passage 45, in response to a rotation position (open degree) of the air mixing door 46.

Because a ratio of an amount of air (warm air amount) passing the heater core 44 to an amount of air (cool air amount) flowing through the bypass passage 45 can be adjusted based on the open degree of the air mixing door 46, a temperature of air which is blown into the passenger compartment can be adjusted.

Temperature-conditioned air is blown out through at least one of the defroster blowing-out port 48, the face blowing-out port 49, the foot blowing-out port 50 and the like, into the passenger compartment to air-condition the passenger compartment and defog the window glass 12 (e.g. windshield) of the vehicle. The defroster blowing-out port 48, the face blowing-out port 49, the foot blowing-out port 50 and the like are arranged at the most downstream side of the air passage defined in the case unit 31.

Next, the operation of the window fog detecting apparatus 10 according to the first embodiment will be described with reference to FIG. 5.

Figure 3:
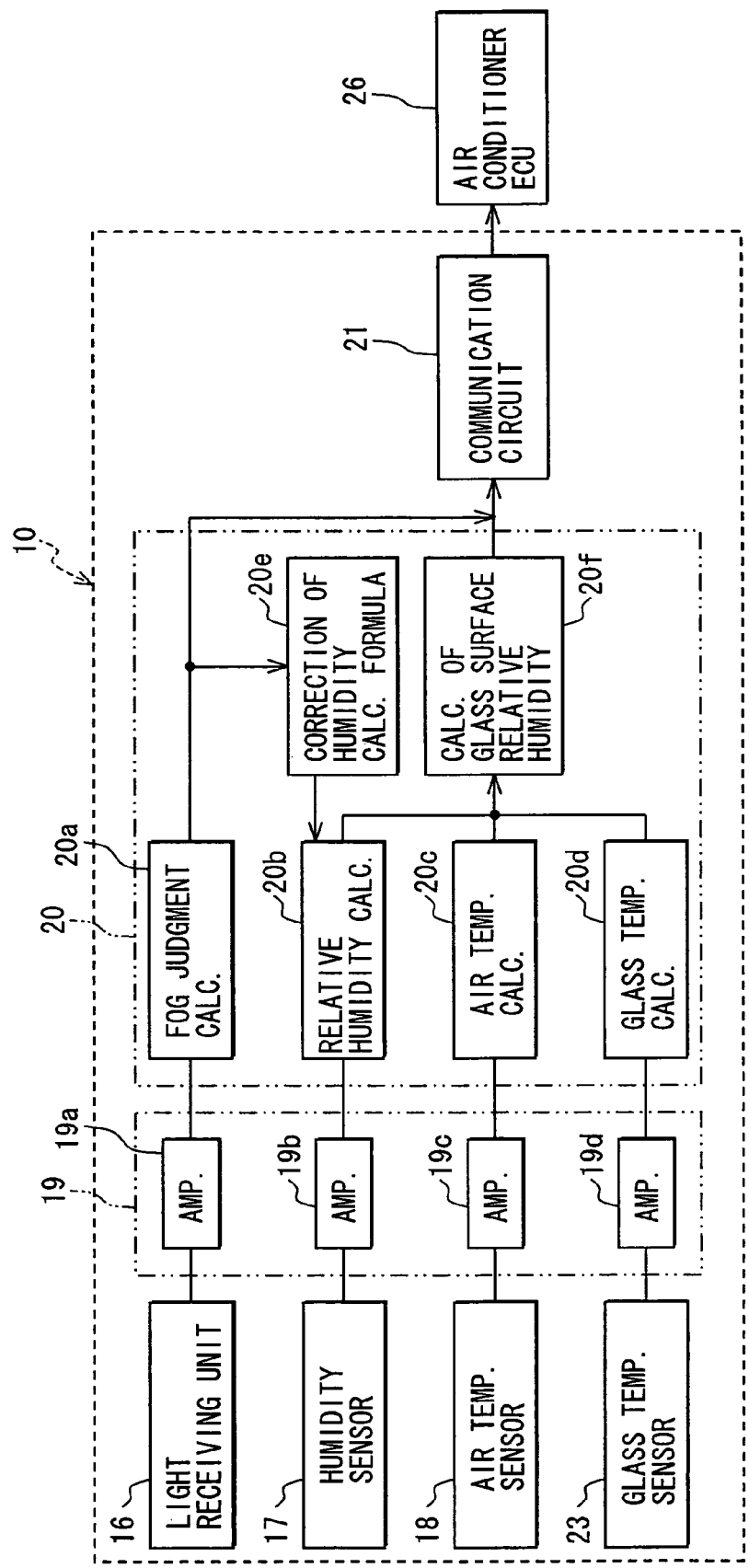
FIG. 3 is a block diagram showing an electrical construction of the window fog detecting apparatus according to the first embodiment.
Figure 5:
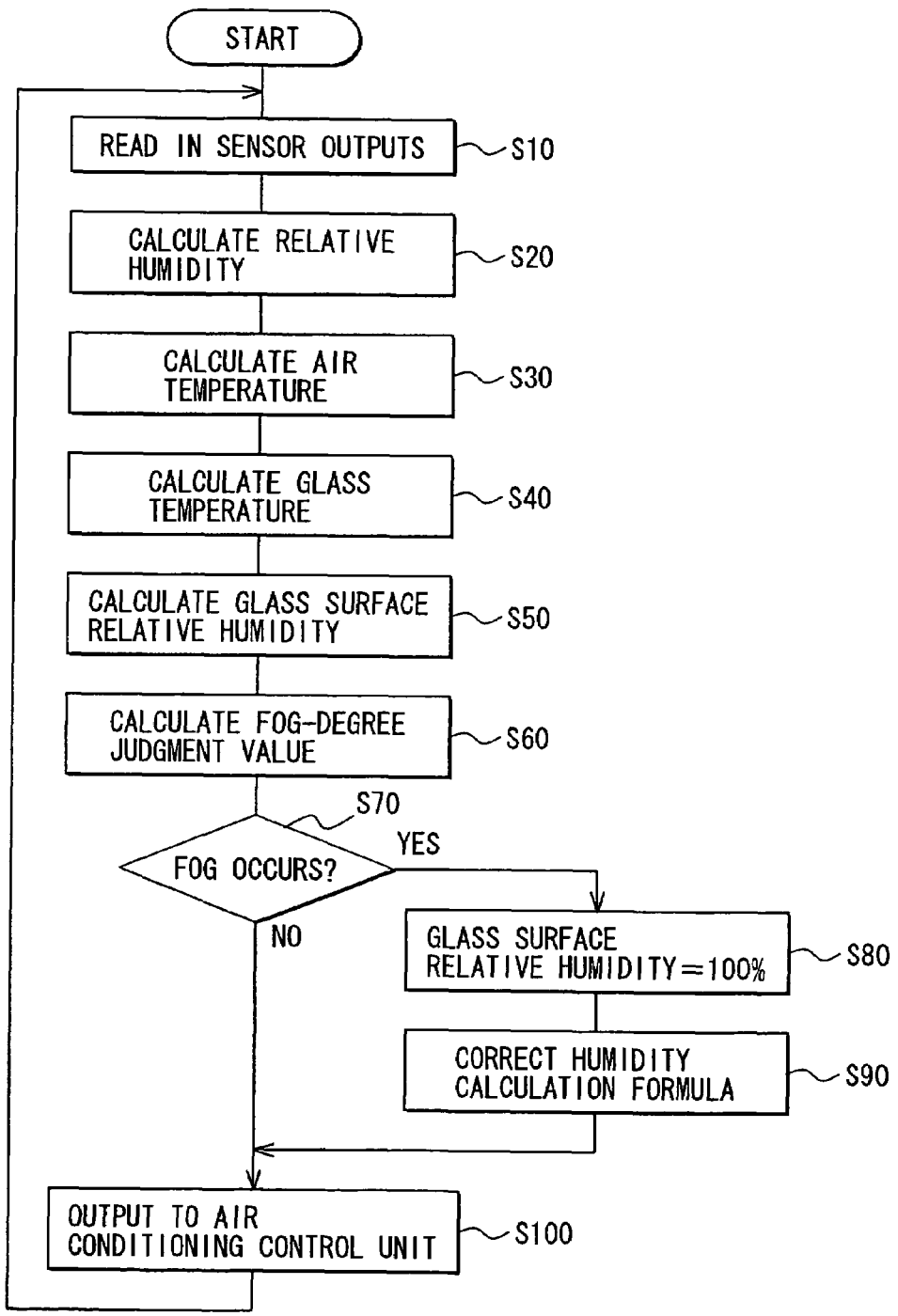
FIG. 5 is a flow chart showing a calculation process executed by a calculation circuit in FIG. 3.

FIG. 5 shows a control routine executed by the calculation circuit 20 shown in FIG. 3. The control routine will be started responding to a driving start of the vehicle or an operation start of the vehicle air conditioner.

First, at step S10, output values (having been amplified by amplifiers 19a-19d) of the sensors 16, 17, 18, 23 shown in FIG. 3 are read in. Then, at step S20 (sensor output correcting unit), a relative humidity RH of inside air (air inside passenger compartment) near the window glass 12 is calculated based on the output value V of the humidity sensor 17.

That is, a predetermined calculation formula (e.g., formula (1)) for converting the output value V of the humidity sensor 17 to the relative humidity RH is beforehand set. Thus, the relative humidity RH can be calculated by applying the output value V to the calculation formula.

$$RH = \alpha V + \beta \quad (1)$$

Wherein α is a control coefficient, and β is a constant.

Thereafter, at step S30, the temperature of inside air near the window glass 12 is calculated by applying the output value of the air temperature sensor 18 to a predetermined calculation formula, which is before set.

Then, at step S40, a window glass temperature (temperature of inner surface 12 of window glass 12) is calculated by applying the output value of the glass temperature sensor 23 to a predetermined calculation formula which is beforehand set.

At step S50, a window glass surface relative humidity RHw (i.e., relative humidity of inner surface 12a of window glass 12) is calculated based on the relative humidity RH, the air temperature and the window glass temperature, which are calculated at steps S20-S40. That is, according to a moist air diagram, the window glass surface relative humidity RHw can be calculated based on the relative humidity RH, the air temperature, and the window glass temperature.

Then, at step S60, a fog-degree judgment value is calculated by applying an output value of the light receiving unit 16 to a predetermined calculation formula which is beforehand set. In the calculation of the fog-degree judgment value, the output value (original value) of the light receiving unit 16 is converted to be suitable for an actual fog degree of the window glass 12.

As described above, the output value (that is, output current of photodiode) of the light receiving unit 16 will decrease due to a fog occurrence on the window glass 12. Thus, the fog-degree judgment value can be calculated as an increase value or a decrease value responding to an increase of the fog degree of the window glass 12.

In the first embodiment, the light emitting unit 15 is set to emit light pulses at a predetermined interval (time interval) which is beforehand set. Therefore, the temperature increase in the case unit 11 due to the heat generation of the light emitting unit 15 can be restricted. Thus, an adverse influence due to the heat generation of the light emitting unit 15 on the temperatures detected by the temperature sensors 18 and 23 and the like can be restricted.

Subsequently, at step S70, it is judged whether or not fog occurs at the window glass 12 based on the fog-degree judgment value calculated at step S60. The judging operation is performed by determining whether or not the fog-degree judgment value obtained in the previous step S60 varies at a speed larger than or equal to a predetermined value.

Specifically, contamination of the window glass 12 due to an adherence of coil components of cigarettes, dust and the like on the window glass 12 advances at a very slow speed for a long time. To the contrary, the fog occurrence (emergence) at the window glass 12 advances at a relative high speed. Therefore, at the step S70, it is determined that fog appears at the window glass 12 in the case where the fog-degree judgment value varies at a speed larger than or equal to the predetermined value, that is, the variation speed of the fog degree judging value is higher than or equal to the predetermined value.

The variation speed of the fog-degree judgment value can be calculated as a variation ratio between the fog-degree judgment values before and after the predetermined interval, at which the light emitting unit 15 emits light pulse.

According to the fog judging operation, a window-fog judgment error which is caused by the window glass contamination due to the adherence of cigarette coil components, dust and the like can be restricted. Thus, fog emergence at the window glass 12 can be substantially judged.

In the case where the fog occurrence is not determined at step S70, step S100 will be performed. On the other hand, in the case where the fog occurrence is determined at step S70, step S80 will be performed. At step S80, the window glass surface relative humidity RHw is set as 100%. That is, the window glass surface relative humidity RHw calculated based on the humidity sensor output value at step S50 is changed into (replaced by) 100%. Then, at step S90 (sensor output correcting unit), a self-correction of the above-described humidity calculation formula (1) is performed.

On the other hand, the air conditioning control unit 26 performs an anti-fog control (described later) with reference to FIG. 6 based on the window glass surface relative humidity RHw. When the relative humidity RH calculated based on the output value of the humidity sensor 17 deviates from the actual relative humidity to a value smaller than the actual relative humidity, fog will appear at the window glass 12 although the anti-fog control is performed.

Therefore, at step S90, the above-described humidity calculation formula (1) is self-corrected to increase the calculation value of the relative humidity RH. Specifically, in the case where the relation between the humidity sensor output value V and the relative humidity RH is expressed by RH=αV+β in the formula (1), a converted relative humidity RH' can be obtained via the moist air diagram where the air temperature is set in response to the window glass surface relative humidity RHw=100%. When RH' is expressed as RH'=αV+β', β'=β−RH+RH' (that is, β'=β+(RH'−RH)) can be obtained.

Because the humidity calculation formula is corrected at step S90, a calculation process of the relative humidity RH approximate to the actual relative humidity can be performed from the succeeding-time operation of step S20.

After step S90, step S100 is performed. At step S100, a final value of the window glass surface relative humidity RHw is outputted to the air conditioning control unit 26. That is, when it is determined that fog occurs at the window glass 12, the window glass surface relative humidity RHw of 100% having been set at step S80 is outputted to the air conditioning control unit 26. To the contrary, in the case where it is determined that fog does not appear at the window glass 12, the window glass surface relative humidity RHw calculated at step S50 is outputted to the air conditioning control unit 26. Moreover, at step S100, the fog-degree judgment value calculated at step S60 is outputted to the air conditioning control unit 26 in addition to the window glass surface relative humidity RHw.

In this case, when a fog occurrence at the window glass 12 is determined based on the output values of the optical type fog detecting sensor (15, 16), the sensor output correcting unit corrects the relative humidity detected by the humidity sensor 17 based on the output values of the optical type fog detecting sensor (15, 16) in the case where there exits a difference about the fog occurrence at the window glass 12 between the relative humidity detected by the humidity sensor 17 and the output values of the optical type fog detecting sensor (15, 16).

As described above, the humidity calculation formula is corrected by a correction of the constant β. Alternatively, the control coefficient α can be also corrected instead of the constant β. Further alternatively, the humidity calculation formula can be also corrected by a correction of both the constant β and the control coefficient α.

Next, an air conditioning control operation based on the window glass surface relative humidity RHw will be described.

Figure 6:
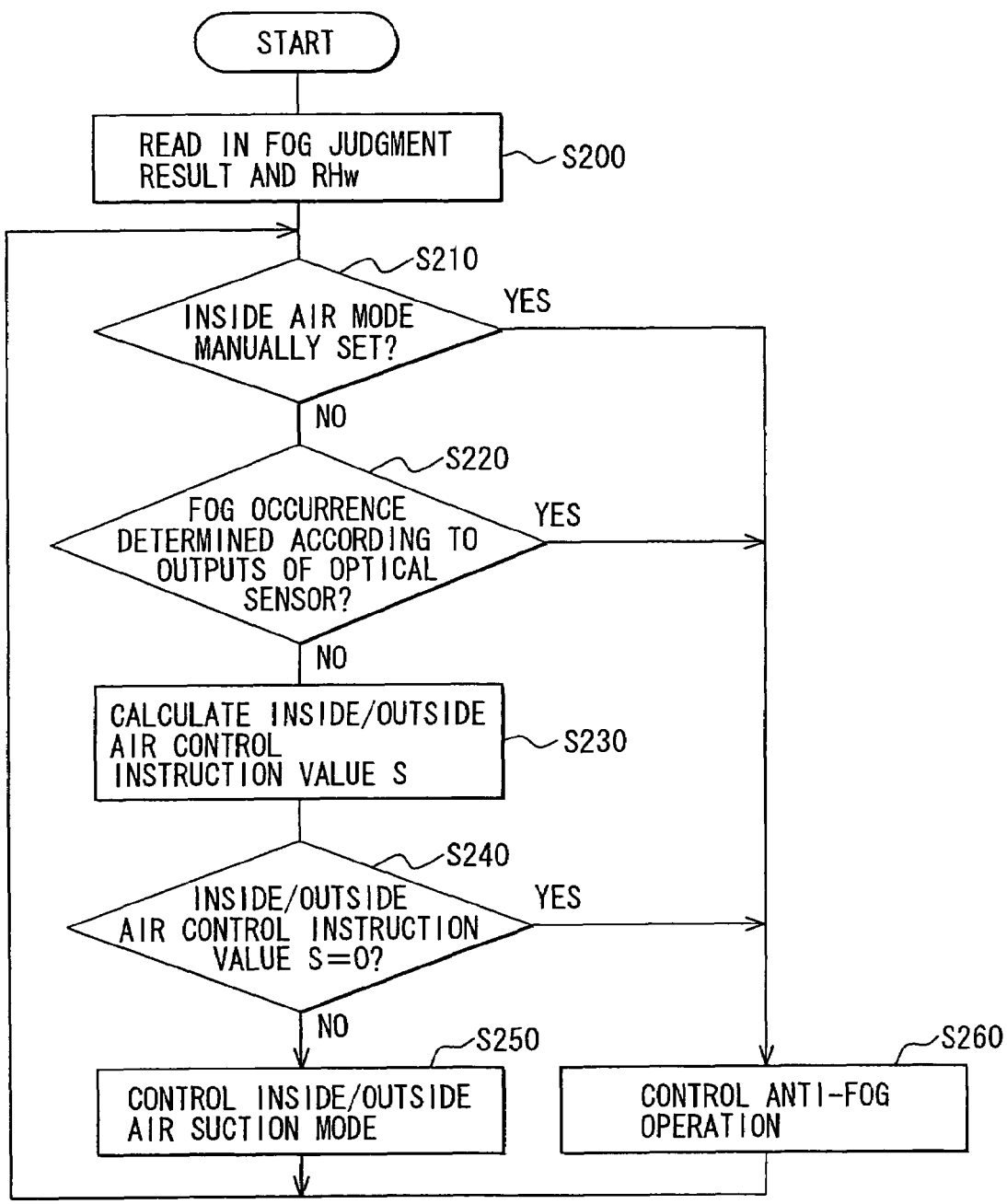
FIG. 6 is a flow chart showing a basic control logic of the air conditioner according to the first embodiment.

FIG. 6 shows a control routine executed by the air conditioning control unit 26. At first, at step S200, the window glass surface relative humidity RHw calculated according to the control routine of FIG. 5 and the result of the window glass fog judging operation defined at step S70 of FIG. 5 are read in.

Then, at step S210, it is judged whether or not the inside/outside air suction mode is manually set as the inside air mode via the inside/outside air selecting switch 73 of the air conditioning operation panel 70. In the case where it is determined that the inside/outside air suction mode is not manually set as the inside air mode (i.e., result of step S210 is "NO"), step 220 will be performed. At step S220, it is further judged whether or not a fog occurrence is determined according to the output values of the optical sensor (light emitting unit 15 and light receiving unit 16) at step S70 shown in FIG. 5. When it is determined that fog does not occur at the window glass 12, an inside/outside air control instruction value S is calculated at step S230.

Figure 7:
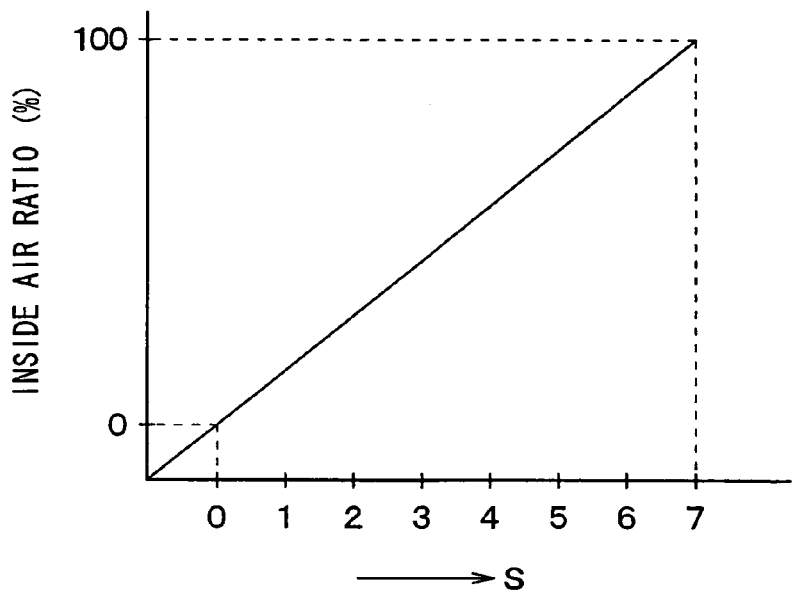
FIG. 7 is a characteristic diagram showing a relation between an inside/outside air control instruction value and an inside air ratio according to the first embodiment.

As shown in FIG. 7, an inside air ratio in air sucked by the air conditioner is determined by the inside/outside air control instruction value S. In this case, the inside air ratio is set as 0% (that is, as outside air mode where 100% of suction air is outside air) in the case of S=0, and the inside air ratio is set as 100% (that is, as inside air mode where 100% of suction air is inside air) in the case of S=7. The inside air ratio sequentially increased when S increases from "1" to "7".

Figure 8:
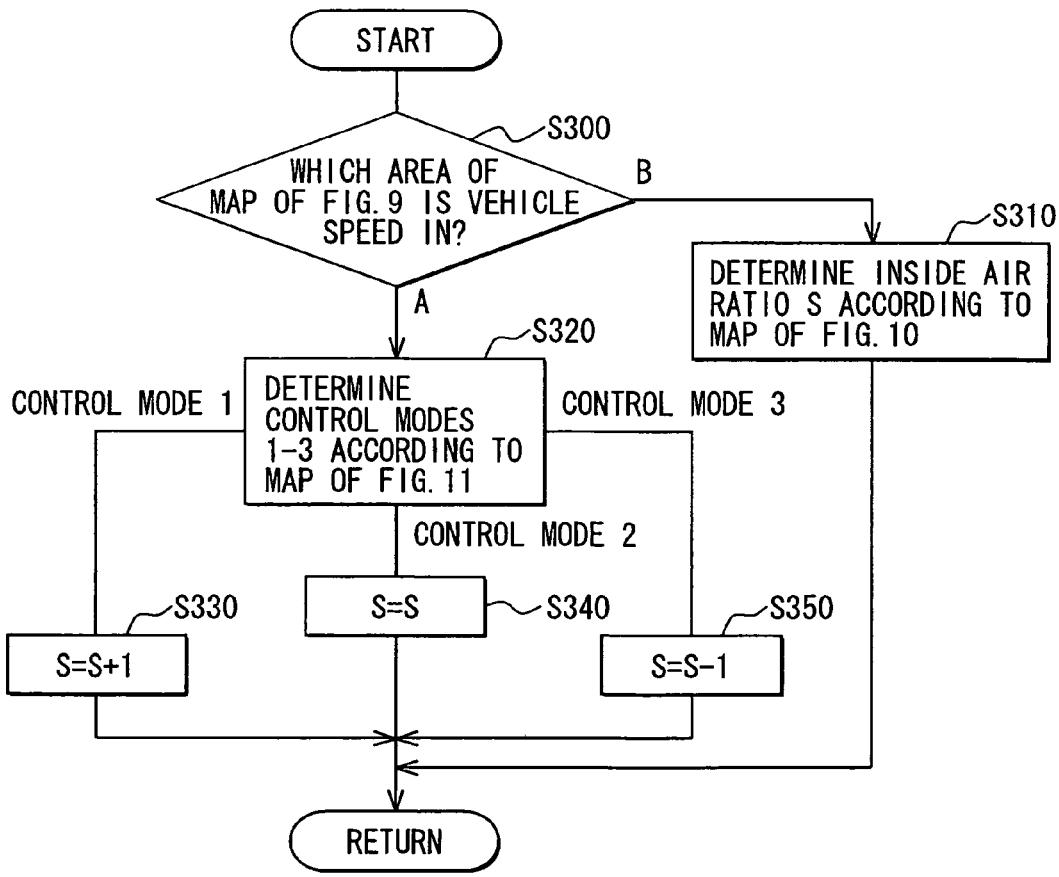
FIG. 8 is a flow chart showing an inside/outside air control logic according to the first embodiment.
Figure 9:
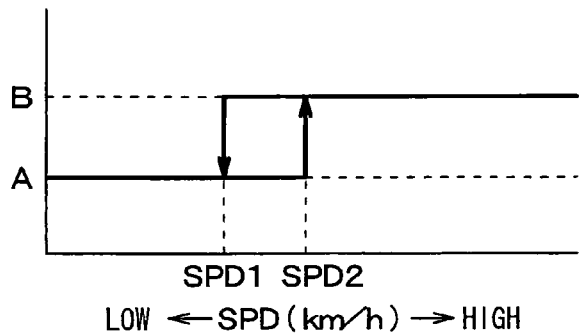
FIG. 9 is a characteristic diagram showing a vehicle speed judging operation in an inside/outside air control according to the first embodiment.

FIG. 8 shows an example of a control routine performed at step S230. At first, at step S300, it is judged which of a low speed area A and a high speed area B of a map shown in FIG. 9 a vehicle speed SPD is in. When it is determined that the vehicle speed SPD is in the high speed area B, the inside/outside air control instruction value S is determined based on the window glass surface relative humidity RHw as indicated in a map of FIG. 10 at step S310.

Figure 10:
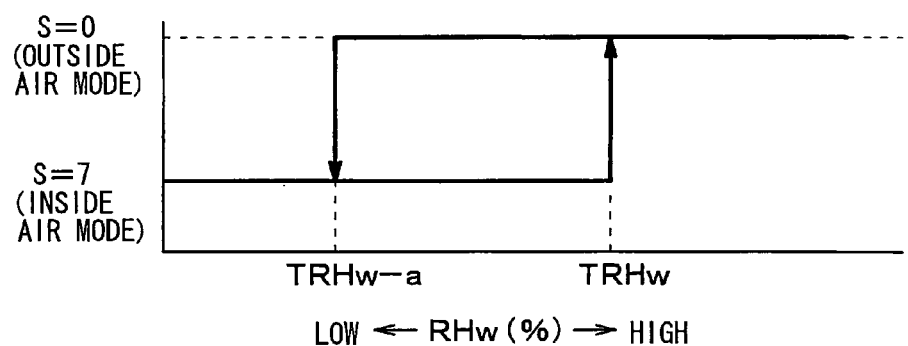
FIG. 10 is a characteristic diagram showing a relation between a window glass surface relative humidity and the inside/outside air control instruction value (inside/outside air suction mode) according to the first embodiment.

That is, referring to FIG. 10, in the case where the window glass surface relative humidity RHw is higher than a predetermined target window glass surface relative humidity TRHw, S is set substantially equal to "0" (that is, outside air mode is set). In the case where the window glass surface relative humidity RHw is lower than (TRHw-a), S is set substantially equal to "7" (that is, inside air mode is set). The target window glass surface relative humidity TRHw is a relative humidity provided with a level capable of sufficiently preventing a frog occurrence (at 85%, for example) at the window glass 12.

Figure 11:
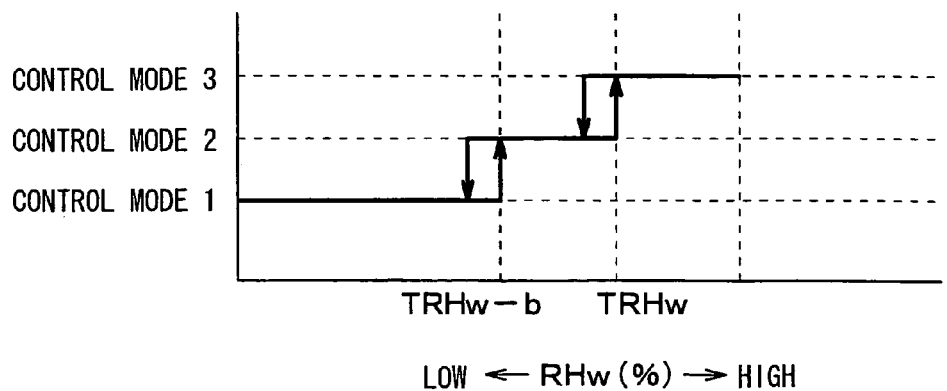
FIG. 11 is a characteristic diagram showing a relation between the window glass surface relative humidity and inside/outside air control modes according to the first embodiment.

On the other hand, when the vehicle speed SPD is located in the low speed area A, control modes 1, 2 and 3 shown in the map of FIG. 11 are chosen based on the window glass surface relative humidity RHw at step S320.

That is, when the window glass surface relative humidity RHw is higher than the predetermined target window glass surface relative humidity TRHw (for example, 85%), the control mode 3 is determined. When the window glass surface relative humidity RHw is located between the target window glass surface relative humidity TRHw and (TRHw-b), the control mode 2 is determined. When the window glass surface relative humidity RHw is lower than (TRHw-b), the control mode 1 is determined.

In the case where the control mode 1 is determined, a control process of S=S+1 is performed at intervals of a predetermined period at step S330. That is, the control process is performed so that the value of the inside/outside air control instruction value S is successively increased by an one-by-one addition of "1" thereto every the predetermined period. Thus, the inside air ratio is provided with a sequential increase with a predetermined rate.

In the case where the control mode 2 is determined, because the window glass surface relative humidity RHw approximates the target window glass surface relative humidity TRHw, a control process of S=S is carried out. That is, the previously calculated value of S is maintained as the value of the inside/outside air control instruction value S at step S340.

In the case where the control mode 3 is determined, a control process of S=S−1 is performed at intervals of a predetermined period at step S350. That is, the value of the inside/outside air control instruction value S is successively decreased by an one-by-one subtraction of "1" therefrom every the predetermined period. Thus, the inside air ratio is provided with a sequential decrease with a predetermined rate.

The predetermined values a and b shown in FIG. 10 and FIG. 11 are provided to set a hysteresis width to avoid a hunting of the inside/outside air control operation.

As described above, referring to FIG. 6, step S240 will be performed after step S230. At step S240, it is judged whether or not the above-described inside/outside air control instruction value S is equal to the value (i.e., S=0) in the case of the outside air mode. When it is determined that the above-described inside/outside air control instruction value S is not equal to 0, step S250 will be performed. At step S250, the position of the inside/outside air switching door 35 is controlled to have the inside air ratio based on the value of the inside/outside air control instruction value S, that is, the inside/outside air suction mode is controlled.

In the inside/outside air suction mode control operation, because the target window glass surface relative humidity TRHW is set substantially equal to an upper limit humidity at which fog does not occur at the window glass 12, the inside/outside air suction mode can be controlled in such a manner that the inside air ratio currently becomes high within a range where fog does not occur at the window glass 12. Therefore, when the heating operation is started during winter or the like, the inside air ratio is increased to reduce a ventilation thermal loss, thus improving a warming-up effect of the heating of the passenger compartment.

On the other hand, in the cases where the judgment results of steps S210, S220, S240 of FIG. 6 become "YES", a necessity of a fog-preventing control operation of the window glass 12 is high and step S260 will be performed. At step S260, the anti-fog control of the window glass 12 is performed.

Figure 12:
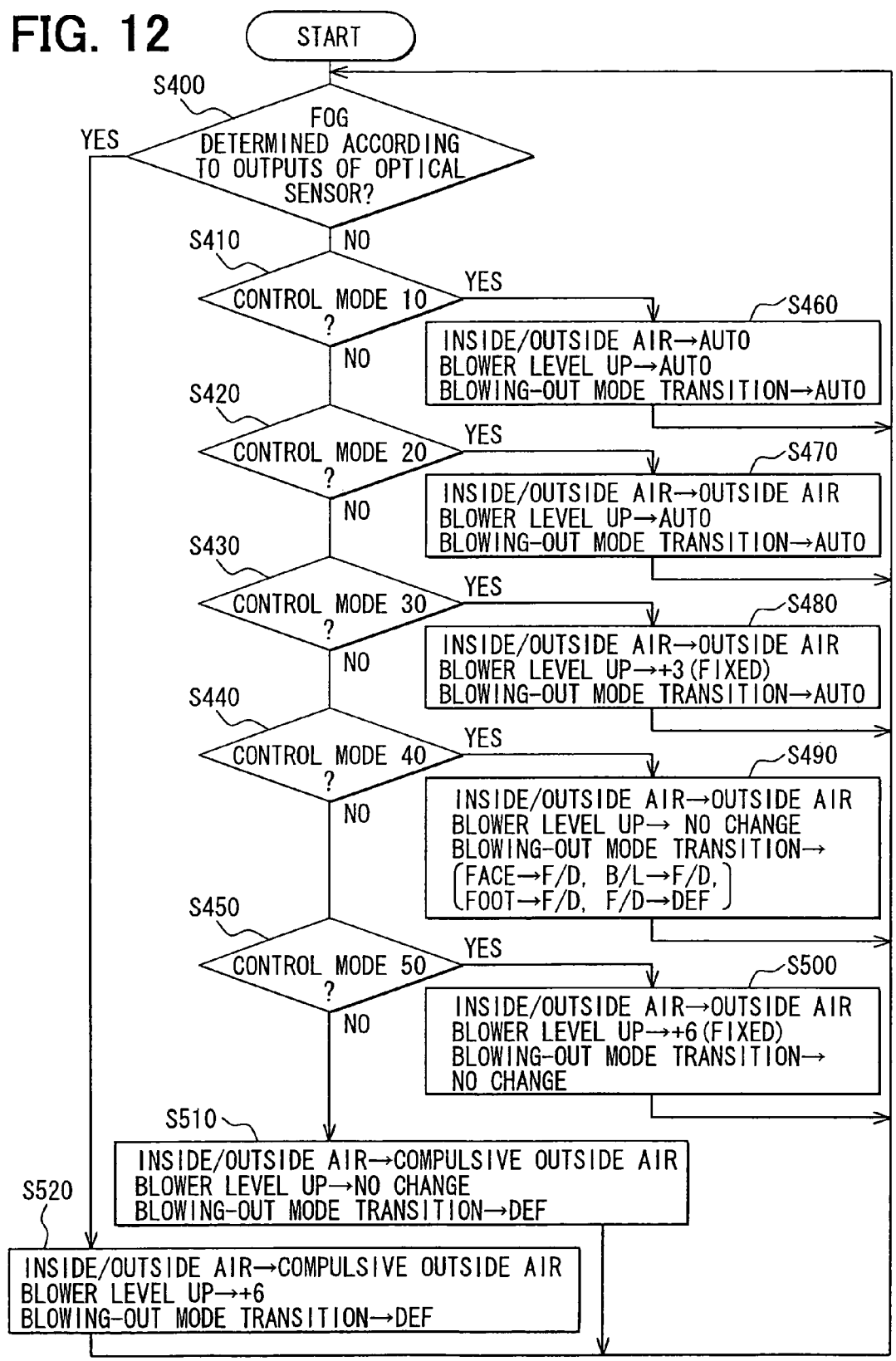
FIG. 12 is a flow chart showing an anti-fog control logic according to the first embodiment.

FIG. 12 shows an example of a control routine of the anti-fog control operation. At first, at step S400, it is judged whether or not the fog occurrence is determined at step S70 shown in FIG. 5. When fog does not occur, the anti-fog control operation defined from step S410 to step S510 is performed.

In the other hand, when fog occurs at the window glass 12, a defogging control mode defined at step S520 is executed. In this case, the inside/outside air suction mode is switched to the outside air mode, and a blower level of the blower 37 is increased by 6 levels. Moreover, the blowing-out mode is switched to the defroster mode. The blower level corresponds to a motor-applying voltage level of the blower 37. Because the air-blowing amount is adjustable in response to an increase/decrease of the motor-applying voltage level, an air-blowing amount level of the blower 37 can correspond to the blower level.

By the operation at step S520, outside air having a low humidity is introduced and heated to become warm air which will be blown-out to the inner surface 12a of the window glass 12 through the defroster blowing-out port 48, and the blowing-out amount of warm air is increased. Thus, the window glass surface relative humidity RHw is quickly lowered, so that fog occurring at the window glass 12 can be removed.

On the other hand, control modes 10-50 will be respectively determined at steps S410-S450, based on the window glass surface relative humidity RHw with reference to FIG.

Figure 13:
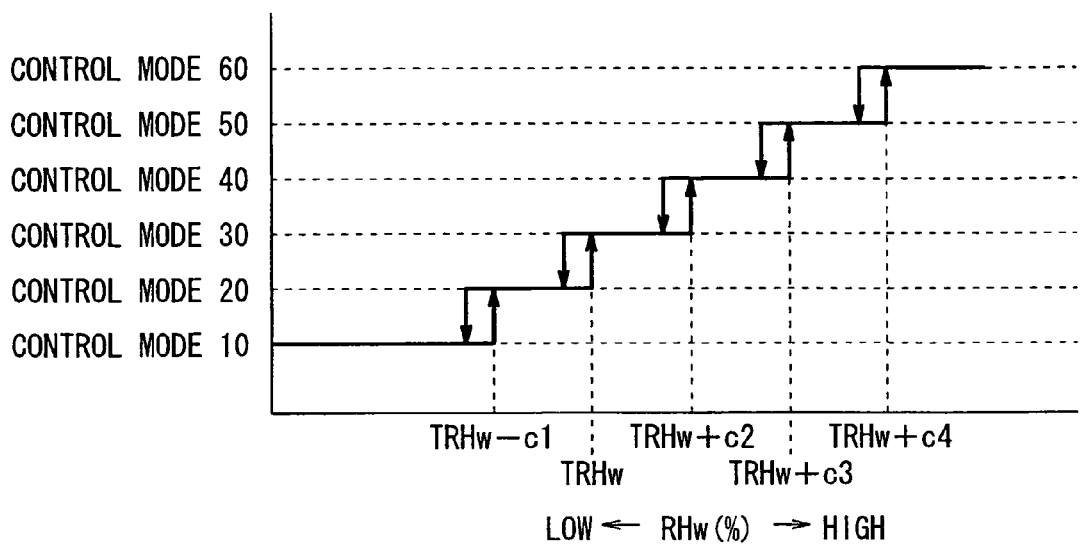
FIG. 13 is a characteristic diagram showing a relationship between the window glass surface relative humidity and anti-flog control modes according to the first embodiment.

13. As shown in FIG. 13, the target window glass surface relative humidity TRHw (for example, 85%) and judgment threshold values (totaling five) are set, and one of six control modes 10-60 is selected based on a change of the window glass surface relative humidity RHw. The five judgment threshold values are set to have an increase/decrease of amounts $c1, c2, c3, c4$ with respect to the target window glass surface relative humidity TRHw. That is, the five judgment threshold values are respectively set as TRHw−$c1$, TRHW, TRHw+$c2$, TRHw+$c3$, and TRHw+$c4$.

As shown in FIG. 12, the control modes 10-60 are respectively executed at steps S460-S510. When the control mode 1 is determined at step S410, the control mode 10 is performed so that the normal automatic control is performed at S460. When the control mode 20 is determined at step S420, the control mode 20 is performed so that the inside/outside air mode is set to be the outside air mode at step S470. When the control mode 30 is determined at step S430, the control mode 30 is performed so that the blower level is increased by three levels at step S480. When the control mode 40 is determined at step S440, the control mode 40 is performed so that the transition of the blowing-out modes is performed at step S490. When the control mode 50 is determined at step S450, the control mode 50 is performed so that the blower level is further increased by three levels at step S500. When the control mode 50 is not determined at step S450, step S510 will be performed. At step S510, the control mode 60 is performed so that the inside air mode is compulsively switched to the outside mode in the case where the inside air mode is manually set.

Referring to FIG. 12, the symbol "AUTO" represents the normal automatic control mode in which controls of the inside/outside air suction mode, the blower level, and the blowing-out mode are normal automatic controls performed based on a target blowing-out temperature TAO of air blown into the passenger compartment. The symbols "Face", "B/L", "Foot", "F/D" and "DEF" respectively represent a face mode in which air is blown out through the face blowing-out port 49, a bi-level mode in which air is blown out through both the face blowing-out port 49 and the foot blowing-out port 50, a foot mode in which air is blown out through the foot blowing-out port 50, a foot defrost mode in which air is blown out through both the foot blowing-out port 50 and the defroster blowing-out port 48, and a defroster mode in which air is blown out through the defroster blowing-out port 48.

The blowing-out mode transition at step S490 (control mode 40) is performed as below. That is, when a blowing-out mode of a control mode before the control mode 40 is the F/D blowing-out mode, the F/D blowing-out mode will be transferred to the DEF blowing-out mode. When the blowing-out mode of the control mode 40 before the control mode 40 is the blowing-out mode other than the F/D blowing-out mode, the blowing-out mode will be transferred to the F/D blowing-out mode. Then, when the blowing-out mode is transferred to the F/D mode in the control mode 40, the F/D mode is maintained even if the state of the control mode 40 is continued.

At steps S460-S500 shown in FIG. 12, when the inside air mode is manually set, the inside/outside air suction mode is kept to be the inside air mode.

According to the anti-fog control operation with reference to FIGS. 12 and 13, the control mode can be sequentially switched from the control mode 10 to the control mode 60 in response to the increase of the window glass surface relative humidity RHw. The RHw-decreasing effects of the control modes 10, 20, 30, 40, 50 and 60 are set become higher in sequence. Therefore, the fog preventing of the window glass can be automatically substantially performed.

Figure 14:
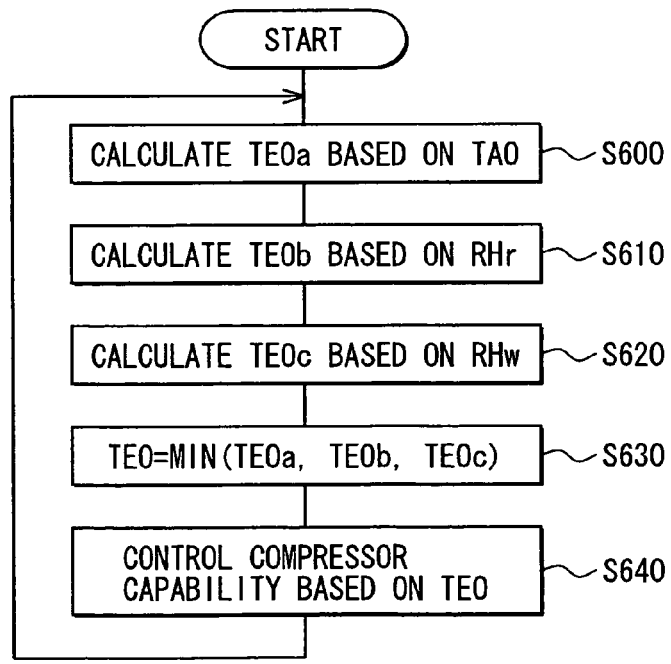
FIG. 14 is a flow chart showing a compressor control logic according to the first embodiment.

Next, the operation of the compressor control according to the first embodiment will be described with reference to FIG. 14. Because the compressor control operation is basically similar to what disclosed in JP-7-179120-A, a summary of the compressor control operation is described.

At first, at step S600, a target evaporator temperature TEOa (that is, target temperature of cooling heat exchanger) used to control the vehicle internal temperature (temperature in passenger compartment) is calculated based on the target blowing-out temperature TAO of air blown into the passenger compartment.

Specifically, the target evaporator temperature TEOa is calculated in such a manner that the passenger compartment evaporator temperature TEOa is increased from a minimum temperature (for example, 3° C.) to a maximum temperature (for example, 11° C.) as the target blowing-out temperature TAO is increased.

The target blowing-out temperature TAO is an interior blowing-out air temperature (i.e., blowing-out air temperature in passenger compartment) which is necessary to maintain the temperature Tr (inside air temperature) of the interior of the passenger compartment at a set temperature Tset, which is set through the temperature setting switch 71. As well known, the target blowing-out temperature TAO can be calculated based on the set temperature Tset, the outside air temperature Tam, the inside air temperature Tr, and the solar radiation amount Ts.

Then, at step S610, a target evaporator temperature TEOb used to control vehicle interior humidity is calculated based on the vehicle interior humidity RHr (humidity in passenger compartment) detected by the humidity sensor 17. The target evaporator temperature TEOb is calculated in such a manner that the vehicle interior humidity RHr is maintained within a predetermined comfortable range, for example, a humidity range from about 50% to about 60%.

Therefore, when the vehicle interior humidity RHr is higher than or equal to, for example, 60%, the value of the temperature TEOb will be changed to the low temperature side. When the vehicle interior humidity RHr is lower than or equal to, for example, 50%, the value of the temperature TEOb will be changed to the high temperature side.

Thereafter, at step S620, a target evaporator temperature TEOc for the sake of the anti-fog control operation is calculated. The temperature TEOc is calculated in such a manner that the anti-fog control operation can be performed based on a cooling (dehumidifying) capability of the evaporator 38.

Specifically, the target evaporator temperature TEOc is set as an evaporator temperature so that the window glass surface relative humidity RHw can be maintained between the target window glass surface relative humidity TRHw of FIG. 11 and the relative humidity (TRHw-b). The target evaporator temperature TEOc can be obtained from the glass temperature, the relative humidity TRHw and (TRHw-b1), and the relative humidity (substantially equal to 95%) of air blown out from the evaporator according to the wet air diagram.

Then, at step S630, the minimum one of the target evaporator temperatures TEOa, TEOb and TEOc is calculated as a final target evaporator temperature TEO. At step S640, the capability control of the compressor 40 is executed based on the final target evaporator temperature TEO, by comparing the target evaporator temperature TEO with the evaporator blowing-out air temperature Te detected by the evaporator temperature sensor 64.

That is, when the evaporator blowing-out air temperature Te is increased to be higher than or equal to the target evaporator temperature TEO, the electromagnetic clutch 40a is energized to actuate the compressor 40 (which becomes ON).

On the other hand, when the evaporator blowing-out air temperature Te is decreased to be lower than or equal to a temperature (TEO-z) which is lower than the target evaporator temperature TEO by a predetermined temperature z (e.g., 1° C.), the compressor 40 is stop (which becomes OFF).

Because the actuation of the compressor 40 is intermittently controlled in the above-described manner, the actual evaporator blowing-out air temperature Te is controlled to become substantially equal to the target evaporator temperature TEO.

Moreover, the target evaporator temperature TEO is set to be the minimum one of the target evaporator temperature TEOa used for the vehicle interior temperature control, the target evaporator temperature TEOb used for the vehicle interior humidity control, and the target evaporator temperature TEOc used for the anti-fog control, the cooling degree of the evaporator is controlled by way of the capability control of the compressor 40 so that the vehicle interior temperature control, the vehicle interior humidity control, and the defogging control can be executed.

The above-described capability control of the compressor 40 is performed to change the operating ratio of the compressor 40 by actuating a fixed capacity type compressor in an intermittent manner. In this case, the fixed capacity type compressor is used as the compressor 40. Alternatively, a variable capacity type compressor can be also used as the compressor 40. In this case, the capability control of the compressor 40 is carried out by changing an exhaust capacity of the variable capacity type compressor.

The term "target evaporator temperature" represents a target value of a cooling degree of the evaporator 38. The cooling degree of the evaporator 38 can be measured based on a fin surface temperature of the evaporator 38 in addition to the above-described evaporator blowing-out air temperature Te.

Second Embodiment

In the above-descried first embodiment, the correction of the humidity calculation formula is described. In this case, the calculated output value of the humidity sensor 17 deviates from the actual humidity to the lower humidity value side, so that fog occurs at the window glass 12 although the anti-fog control is performed by the vehicle air conditioner.

According to a second embodiment of the present invention, the humidity calculation formula is corrected in the case where the calculated output value of the humidity sensor 17 deviates from the actual humidity to a higher humidity value side.

In the case where the calculated output value of the humidity sensor 17 deviates from the actual humidity to the higher humidity value side, the effect of the anti-fog control operation by the air conditioner can be ensured. However, this may cause a problem that the inside air ratio is unnecessarily lowered and the ventilation heat loss is increased. Moreover, the capability of the compressor is unnecessarily increased so that the power of the compressor is uselessly increased. Therefore, it is not preferable in a practical use, for the calculated output value of the humidity sensor 17 to deviate from the actual humidity to the higher humidity value side.

On the other hand, when a passenger manually operates the air conditioning switch 74 of the air conditioning operation panel 70 to the OFF position, the air conditioning control unit 26 cuts off the supply of the electric power to the electromagnetic clutch 40a of the compressor 40, so that the compressor 40 is compulsorily stopped. As a result, the cooling dehumidifying capability of the evaporator 38 is also compulsorily stopped. Thus, the vehicle interior relative humidity RHr may increase, so that fog occurs at the window glass 12.

Similarly, when the passenger manually operates the inside/outside air selecting switch 73 of the air conditioning operation panel 70 to the inside air mode position, the air conditioning control unit 26 controls the inside/outside air switching door 35 via the servo motor 36 to the inside air mode position (that is, outside air introduction port 34 is completely closed and inside air introduction port 33 is completely opened). Therefore, because the inside air having an absolute humidity higher than that of the outside air is recirculated to air-condition the passenger compartment, the vehicle interior relative humidity RHr is increased and fog may occur on the window.

According to the second embodiment, in the case where fog occurs at the window glass 12 due to the manual operation by the passenger, the commencement of the anti-fog control is delayed until the fog occurrence at the window glass 12 is judged based on the calculation value of the fog judgment calculation circuit 20a even when the glass surface relative humidity RHw exceeds the threshold value (TRHw of FIG. 11) of the anti-fog control. The fog judgment calculation circuit 20a calculates the output value of the optical type fog detecting sensor (light emitting and receiving units 15, 16).

Then, when the fog occurrence at the window glass 12 is determined based on the calculation value of the fog judgment calculation circuit 20a, the glass surface relative humidity RHw is set as 100% as described at step S80 of FIG. 5 and the humidity calculation formula is corrected at step S90.

As described above, in the case where the calculated output value of the humidity sensor 17 deviates to the higher humidity value side from the actual humidity, the effect (safety rate) of the anti-fog control operation becomes high and the anti-fog control is executed at an earlier timing. Therefore, fog will not occur at the window glass 12 in principle. In this case, the humidity calculation formula can be corrected by utilizing the chance that fog occurs at the window glass 12 due to the manual operation of the passenger, even when the calculated output value of the humidity sensor 17 deviates to the higher humidity value side from the actual humidity.

Third Embodiment

In the above-described second embodiment, the correction method in the case where fog occurs due to the manual operation of the passenger is provided. According to a third embodiment of the present invention, a similar correction can be carried out when a heating operation is started up at a low temperature.

In the case where the outside air temperature is low, for example, in winter, a temperature of the engine cooling water is lowered when the vehicle is parked (that is, engine is stopped). Therefore, a warming-up control may be performed. That is, when the air conditioner is started at the subsequent actuation of the engine, conditioned air is not blown out until the temperature of the engine cooling water becomes higher than or equal to a predetermined value.

Because conditioned air is not blown out in the warming-up control, fog may occur during the warming-up control so that the humidity calculation formula can be corrected.

In the case where fog occurs at the window glass 12 due to the delayed blowing-out of conditioned air by the air conditioner, a comfortable feeling of the passenger will be deteriorated due to a blowing-out of conditioned air. Thus, it is acceptable for the passenger, that the anti-fog control is executed after the fog occurrence at the window glass 12 has been determined based on the outputs of the optical type fog detecting sensor (light receiving and emitting units 15, 16).

Thus, in the case where the temperature of the engine cooling water is lower than a threshold value for the blowing-out of conditioned air, the threshold value (TRHw of FIG. 11) for the anti-fog control is increased, and the commencement of the anti-fog control is delayed until the fog occurrence at the window glass 12 is determined based on the calculation value of the fog judgment calculation circuit 20a.

Then, when the fog occurrence at the window glass 12 is determined based on the calculation value of the fog judgment calculation circuit 20a, the glass surface relative humidity RHw is set 100% as described at step S80 of FIG. 5 and the correction of the humidity calculation formula is carried out.

According to the third embodiment, the humidity calculation formula can be corrected by utilizing the chance that fog occurs at the window glass 12 during the start delay control (warming-up control) in the case of the low temperature of the engine cooling water, even when the calculated output value of the humidity sensor 17 deviates to the higher humidity value side from the actual humidity.

Fourth Embodiment

In the first embodiment, the humidity sensor 17, the light emitting unit 15 and the light receiving unit 16 are mounted at the same circuit board 14. Alternatively, according to a fourth embodiment of the present invention, the humidity sensor 17 can be also mounted at a circuit board different from that where the light emitting unit 15 and the light receiving unit 16 are mounted.

In this case, even when the optical type fog detecting sensor (which is constructed of light emitting unit 15 and light receiving unit 16) and the humidity sensor 17 are mounted at the different circuit boards, these circuit boards can be accommodated in the same case unit 11 and integrated with each other.

Fifth Embodiment

In the first embodiment, the humidity sensor 17, the light emitting unit 15 and the light receiving unit 16 are mounted at the same circuit board 14 within the same case unit 11. Alternatively, according to a fifth embodiment of the present invention, the optical type fog detecting sensor and the humidity sensor 17 can be also respectively arranged in different places.

For example, in the case where the window fog detecting apparatus 10 is used for the air conditioner for the vehicle (e.g., automobile), the inside air sensor 62 (referring to FIG. 4) for detecting the vehicle interior temperature Tr (temperature of air in passenger compartment) can be arranged in the vicinity of the instrument panel disposed in the passenger compartment to detect a typical temperature in the passenger compartment. The humidity sensor 17 can be arranged near the instrument panel (that is, similar to inside air sensor 62) and integrated with the inside air sensor 62. The optical type fog detecting sensor can be arranged on the inner surface of the windshield of the vehicle.

According to the fifth embodiment, because the inside air sensor 62 can function as the air temperature sensor 18 described in the first embodiment, the air temperature sensor 18 can be omitted.

Sixth Embodiment

In the first embodiment, the light emitting unit 15 is constructed of the light-emitting diode, and the light receiving unit 16 is constructed of the photodiode. The light emitting unit 15 and the light receiving unit 16 constitute the optical type fog detecting sensor. According to a sixth embodiment of the present invention, the light emitting unit 15 and the light receiving unit 16 can be also respectively constructed of an infrared light emitting unit and an infrared light receiving unit.

In this case, because the infrared light receiving unit can detect a temperature of an detection object based on a receiving amount of infrared light reflected by the detection object, the infrared light receiving unit is also named an IR sensor. Therefore, according to the sixth embodiment, the infrared light emitting unit can also emit pulse lights at a predetermined interval.

Thus, when the infrared light emitting unit emits the infrared light, fog occurring at the window glass 12 is detected based on the light receiving amount of the infrared light receiving unit. On the other hand, when the infrared light emitting unit does not emit infrared light (that is, infrared light emitting unit is turned off), infrared light radiated from the window glass 12 is received by the infrared light receiving unit so that the temperature of the window glass 12 is detected based on the light receiving amount of the infrared light receiving unit.

Because the infrared light receiving unit of the optical type fog detecting sensor can detect the temperature of the window glass, the glass temperature sensor 23 can be omitted.

Seventh Embodiment

In the first embodiment, the calculation circuit 20 is mounted at the circuit board 14 which is arranged within the case unit 11 of the fog detecting apparatus 10. Alternatively, according to a seventh embodiment of the present invention, the air conditioning control unit 26 can be also additionally provided with the function of the calculation circuit 20 so that the calculation circuit 20 can be omitted.

Eighth Embodiment

In the first embodiment, when the fog emergency is determined at step S70 of FIG. 5, the window glass surface relative humidity RHw calculated based on the output value of the humidity sensor 17 is compulsorily changed into 100% (at step S80). Thereafter, the self-correction of the humidity calculation formula (1) is carried out at step S90.

Alternatively, according to an eighth embodiment of the present invention, for example, after the fog occurrence is determined at step S70, the multiple output values of the humidity sensor 17 can be memorized for multiple times and the self-correction of the humidity calculation formula (1) can be executed by using an average of the output values (which are memorized for multiple times) of the humidity sensor. In this case, at least one of the constant $\beta$ and the coefficient $\alpha$ is corrected.

Ninth Embodiment

In the above-described embodiments, the humidity calculation formula is corrected to restrict an accuracy deterioration of the humidity detection due to a durability deterioration and the like of the humidity sensor 17. According to a ninth embodiment of the present invention, an accuracy deterioration of the fog-degree judgment due to a durability deterioration and the like of the light emitting unit 15 is restricted.

Figure 15:
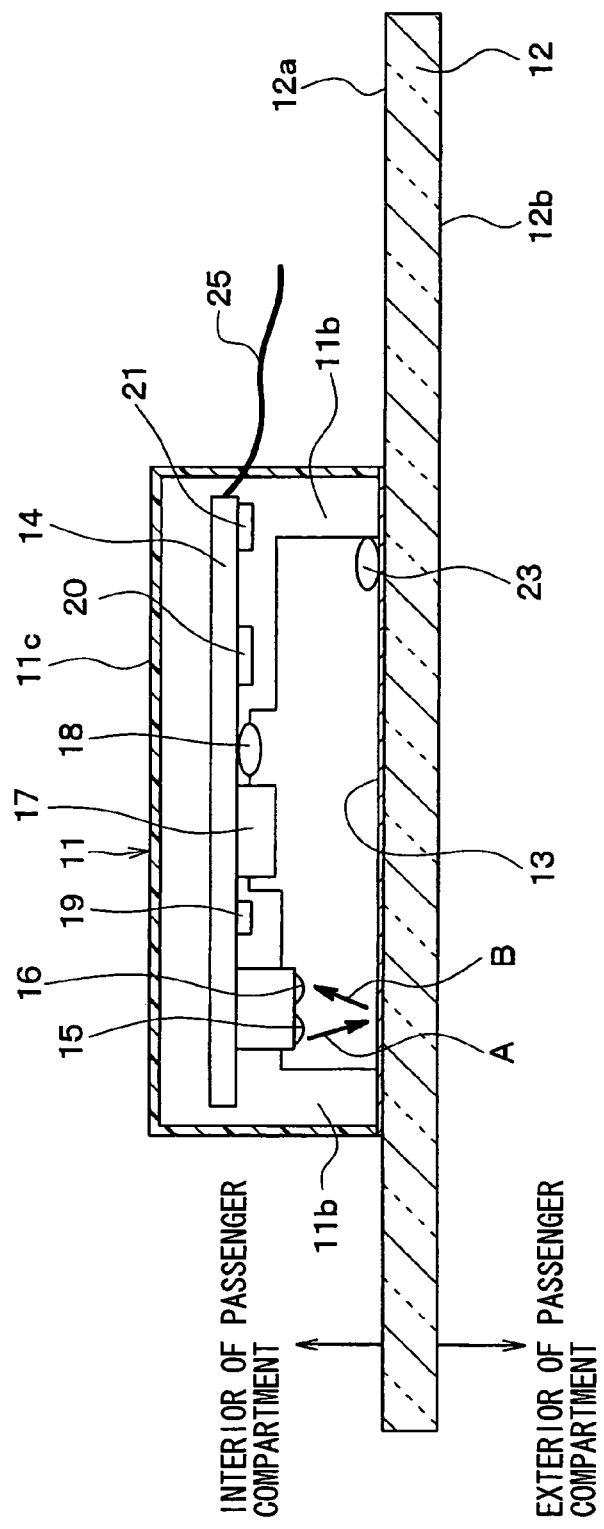
FIG. 15 is a schematic cross-sectional view showing a window fog detecting apparatus according to a ninth embodiment of the present invention.

FIG. 15 shows the window fog detecting apparatus 11 according to the ninth embodiment. In this case, the light emitting unit 15 and the light receiving unit 16, which constitute the optical type fog detecting sensor, are positioned directly adjacent to each other.

Specifically, similar to the first embodiment, the light emitting unit 15 and the light receiving unit 16 are respectively constructed of the light-emitting diode and the photodiode. Projection light A from the light emitting unit 15 is reflected by the lightproof film 13 provided on the inner surface 12a of the window glass 12, and the reflection light B is received by the light receiving unit 16.

The luminance of the light emitting unit 15 may be lowered due to a durability deterioration and the like thereof so that the projection light A of the light emitting unit 15 is reduced. Thus, the reflection light B will decrease.

Moreover, the reflection surface (which is surface of lightproof film 13 in this embodiment) of the window glass 12 can be contaminated by the coil components of cigarettes, dust and the like which adheres to the reflection surface, in addition to the fog occurrence. Therefore, light is scattered so that the reflection light B projected toward the light receiving unit 16 is decreased.

Furthermore, a forward voltage (Vf) of the light emitting diode of the light emitting unit 15 has a temperature characteristic that the forward voltage is lowered due to an increase of an ambient temperature. Thus, the forward voltage (Vf) is lowered at a high temperature so that the projection light A is decreased. Therefore, the reflection light B is reduced.

Because the reflection light B may be reduced due to the above-described reasons, the light receiving amount of the light receiving unit 16 will decrease similar to the case where fog occurs at the window glass 12. If the occurrence of fog at the window glass 12 is judged only based on the decrease of the reflection light B (light receiving amount), an erroneous conclusion of the fog occurrence will be made even when fog does not occur at the window glass 12.

Therefore, according to the ninth embodiment, a fog-degree judgment value Fw is calculated based on a ratio (B/A) of the reflection light B to the projection light A. Moreover, the calculation formula of the fog-degree judgment value Fw is corrected based on a light amount normalizing process for normalizing the reflection light B by the projection light A when fog does not occur at the window glass 12. Thus, the deterioration of the fog-degree judging accuracy due to the reflection light reduction caused by the durability deterioration and the like of the light emitting unit 15 and the contamination of the window glass 12, can be restricted.

Specifically, the calculation formula of the fog-degree judgment value Fw is corrected based on the light amount normalizing process in such a manner that the ratio (B/A) of the reflection light B to the projection light A becomes equal to 1 (that is, fog does not occur at window glass 12) even if the reflection light B is actually less than the projection light A at the time when the process is executed.

If fog actually occurs at the window glass 12 after the correcting process of the calculation formula is executed, the reflection light B decreases as compared with that when the correcting process of the calculation formula is executed, so that the fog-degree judgment value Fw becomes smaller than 1 and is decreased to be smaller than a predetermined threshold value. Thus, the fog occurrence at the window glass 12 can be substantially determined.

Furthermore, the calculation and the judgment of the fog degree can be prohibited, in the case where the temperature is higher than the predetermined temperature so that the projection light A decreases due to the temperature characteristic of the light emitting unit 15. The fog judgment is performed only when the temperature is lower than or equal to the predetermined temperature. Thus, the decrease of the projection light A due to the temperature characteristic of the light emitting unit 15 at the high temperature can be restricted.

The predetermined temperature corresponds to, for example, an outside air temperature (e.g., about 35° C.) in midsummer. In this case, the window glass 12 also has a high temperature. Because the temperature of the window glass 12 is sufficiently higher than the dew-point temperature of the vehicle interior air, fog will not occur at the window glass 12. Therefore, even when the fog degree judgment is prohibited at the temperature higher than the predetermined temperature, no practical problem is caused.

Because the use of the light emitting unit 15 is prohibited at the high temperature, the high temperature deterioration of the light emitting unit 15 can be restricted, and the accumulation use time of the light emitting unit 15 can be reduced. Therefore, the durability deterioration of the light emitting unit 15 can be substantially restricted.

Next, the operation of the window fog detecting apparatus 11 according to the ninth embodiment will be described with reference to FIG. 16 which corresponds to FIG. 5. The explanations of the processes shown in FIG. 16 having the same reference numerals with those in FIG. 15 are omitted.

After step S50, step S110 will be performed. At step S110, it is judged whether or not the air temperature calculation value calculated at step S30 is smaller than or equal to a predetermined value (e.g., about 35° C.). The air temperature corresponds to the vehicle interior air temperature near the window glass 12 and the ambient temperature of the optical type fog detecting sensor (which is constructed of light emitting unit 15 and light receiving unit 16). The predetermined value used at step S110 corresponds to the temperature (e.g., about 35° C.) of outside air in midsummer or the like.

In the case where it is determined that the air temperature calculation value calculated at step S30 is smaller than or equal to the predetermined value (that is, judgment result of step S110 is "YES"), fog possibly occurs at the window glass 12. Thus, at step S120, the optical type fog detecting sensor (15, 16) becomes ON. Specifically, similar to the first embodiment, the light emitting diode of the light emitting unit 15 emits light pulses at the predetermined interval, and the reflection light B reflected by the surface of the window glass 12 is received by the light receiving unit 16.

Then, at step S60a, the fog-degree judgment value Fw is calculated based on the ratio (B/A) of the reflection light B to the projection light A. Specifically, the judgment value Fw is calculated in accordance with a calculation formula of Fw=γ·(B/A), wherein γ is a control coefficient. As described later, the control coefficient γ is self-corrected at intervals of a predetermined period so that Fw becomes equal to 1 in the case where fog does not occur at the window glass 12. Therefore, the fog-degree judgment value Fw is calculated to be substantially equal to 1, when fog does not occur at the window glass 12.

As described above, when fog occurs at the surface of the window glass 12, the reflection light B is reduced so that the judgment value Fw becomes smaller than about 1.

The reflection light B is calculated based on the output value (light receiving amount) of the light receiving unit 16 at the above-described calculation formula. Moreover, because the projection light A has a proportional relationship with the forward current of the light emitting diode of the light emitting unit 15, the projection light A can be calculated based on the forward current.

Thereafter, at step S70a, it is determined whether or not fog occurs at the window glass 12 based on the judgment value Fw. Specifically, a value which is smaller than 1 by a predetermined value is set as a threshold value for the judgment value Fw. In the case where the judgment value Fw is smaller than or equal to the threshold value, it is determined that fog occurs. In the case where the judgment value Fw is larger than the threshold value, it is determined that fog does not occur.

In the case where it is determined that fog occurs at the window glass 12, similar to the first embodiment, the processes defined at step S80 and step S90 are executed, and then the output to the air conditioning control unit 26 is performed at step S100.

In the case where it is determined that fog does not occur at the window glass 12, step S130 will be performed after step S70a. At step S130, it is judged whether or not a predetermined period has elapsed from the time when the preceding correction of the fog-degree judgment value calculating formula was performed.

Specifically, the time (year, month, day) when the preceding correction of the fog-degree judgment value calculating formula is performed at step S140 (described later) is memorized, and it is judged whether nor not the predetermined period (for example, 30 days) has elapsed from the time of the preceding correction. Alternatively, it can be also judged whether or not it is a specific day of every month (for example, first day of every month) based on a calendar function of the computer.

In the case where it is determined that the predetermined period has not elapsed from the time when the preceding correction of the fog-degree judgment value calculating formula was performed (that is, judgment result of step S130 is "NO"), step S100 will be performed.

On the other hand, in the case where it is determined that the predetermined period has elapsed from the time of the preceding correction of the fog-degree judgment value calculating formula (that is, judgment result of step S130 is "YES"), the fog-degree judgment value calculating formula is corrected at step S140 based on the above-described light amount normalizing process for normalizing the reflection light B by the projection light A.

Specifically, in the above-described calculation formula of $Fw=\gamma \cdot (B/A)$, the control coefficient $\gamma$ is corrected so that Fw is substantially equal to 1. Therefore, as long as the light amount of the reflection light B is equal to that of the reflection light B at the time when the above-described correction is performed, the fog-degree judgment value Fw at step S130 is maintained to be about 1. Thus, at step S70a, it is substantially determined that fog does not occur.

When fog occurs at the window glass 12, the reflection light B is decreased so that the fog-degree judgment value Fw becomes smaller than 1. Then, at step S70a, because the judgment value Fw becomes smaller than the above-described predetermined threshold value, it can be substantially determined that fog occurs.

Because the contamination of the reflection surface of the window glass 12 due to the adherence of the oil components of cigarettes and the like progresses very slowly, it is unnecessary to frequently perform the above-described correcting process of the calculating formula (at step S140). In the ninth embodiment, at step S130, only in the case where it is determined that the predetermined period (for example, 30 days) has elapsed from the time of the preceding correction, the above-described calculation formula is corrected.

According to the ninth embodiment, the optical type fog detecting accuracy can be properly maintained for a long duration without being influenced by the decease of the projection light A due to the deterioration of the durability of the light emitting unit 15, and the decrease of the reflection light B due to the contamination of the reflection surface of the window glass 12 which is caused by the adherence of the oil components of cigarettes and the like to the reflection surface.

Moreover, because the fog judging process is performed only when the ambient temperature is lower than or equal to the predetermined temperature (for example, 35° C.), the influence of the temperature characteristic that the luminance of the light emitting unit 15 lowers at the high temperature can be avoided. Moreover, because the fog judging process is performed only when the ambient temperature is lower than or equal to the predetermined temperature, the high-temperature deterioration of the light emitting unit 15 can be restricted, and the accumulation use time of the light emitting unit 15 is reduced so that the lifetime of the light emitting unit 15 can be prolonged.

According to the ninth embodiment, in the case where the fog-degree judgment value Fw is calculated based on the calculation formula of $Fw=\gamma \cdot (B/A)$, the control coefficient $\gamma$ is corrected so that Fw is equal to about 1. Alternatively, in the case where the fog-degree judgment value Fw is calculated based on other calculation formula, for example, $Fw=\gamma \cdot (B/A)+\delta$ ($\delta$ is constant), the constant $\delta$ can be corrected so that Fw is equal to about 1. More alternatively, both the control coefficient $\gamma$ and the constant $\delta$ can be also corrected so that Fw is equal to about 1. In this case, when the control coefficient $\gamma$ and/or the constant $\delta$ are corrected, the correction can be performed so that Fw approximates to 1.

Other Embodiments

Although the present invention has been fully described in connection with the preferred embodiments thereof with reference to the accompanying drawings, it is to be noted that various changes and modifications will become apparent to those skilled in the art.

The window fog detecting apparatus 11 according to the present invention can be also mounted at a rear window glass or the like of the vehicle to detect a fog occurrence thereat. Moreover, the present invention can be also suitably used for fog-detecting a window of a device, a building or the like.

Furthermore, in the ninth embodiment, the light emitting unit 15 is constructed of the light emitting diode, and the light receiving unit 16 is constructed of the photodiode. However, the light emitting unit 15 can be also constructed of, for example, the infrared light emitting unit described in the sixth embodiment. The light receiving unit 16 can be also constructed of, for example, the infrared light receiving unit described in the sixth embodiment.

Such changes and modifications are to be understood as being in the scope of the present invention as defined by the appended claims.

What is claimed is:

1. A window fog detecting apparatus comprising:
    an optical type fog detecting sensor for optically detecting fog occurring at a window glass;
    a humidity sensor for detecting a relative humidity of air at an interior side of the window glass for the sake of an anti-fog control which is performed to prevent fog from occurring at the window glass; and
    a sensor output correcting unit, wherein
    when a fog occurrence at the window glass is determined based on the output values of the optical type fog detecting sensor, the sensor output correcting unit corrects the relative humidity detected by the humidity sensor based on output values of the optical type fog detecting sensor in the case where there exits a difference about the fog occurrence at the window glass between the relative humidity detected by the humidity sensor and the output values of the optical type fog detecting sensor.

2. The window fog detecting apparatus according to claim 1, further comprising:
- an air temperature sensor for detecting a temperature of air at the interior side of the window glass;
- a glass temperature sensor for detecting a temperature of the window glass; and
- a glass surface relative humidity calculating unit for calculating a relative humidity of an inner surface of the window glass based on output values of the humidity sensor, the air temperature sensor and the glass temperature sensor, the inner surface being positioned at the interior side of the window glass.

3. The window fog detecting apparatus according to claim 1, further comprising
- a relative humidity calculating unit for calculating the relative humidity of air at the interior side of the window glass based on the output value of the humidity sensor according to a predetermined calculation formula, wherein
- when it is determined that fog occurs at the window glass based on the output value of the optical type fog detecting sensor, the sensor output correcting unit corrects the calculation formula so that a calculation value of the relative humidity calculating unit becomes equal to a relative humidity at an interior air temperature at which a relative humidity of an inner surface of the window glass is 100%, the interior air temperature being a temperature of air at the interior side of the window glass and the inner surface being at the interior side of the window glass.

4. The window fog detecting apparatus according to claim 2, wherein:
- the optical type fog detecting sensor includes a light emitting unit and a light receiving unit; and
- the light emitting unit, the light receiving unit, the humidity sensor, the air temperature sensor, and the glass temperature sensor are integrated with the inner surface of the window glass.

5. The window fog detecting apparatus according to claim 4, further comprising
- a circuit board, at which the light emitting unit, the light receiving unit, the humidity sensor and the air temperature sensor are arranged.

6. The window fog detecting apparatus according to claim 4, further comprising
- a case unit which is arranged on the inner surface of the window glass and provided with a communication opening portion communicated with an space at the interior side of the window glass, wherein
- the light emitting unit, the light receiving unit, the humidity sensor, the air temperature sensor and the glass temperature sensor are accommodated in the case unit.

7. The window fog detecting apparatus according to claim 6, wherein
- the case unit has at least one positioning portion for defining an interval between the inner surface of the window glass and each of the light emitting unit and the light receiving unit.

8. The window fog detecting apparatus according to claim 4, further comprising
- a lightproof film which is made of a light-tight material and adheres to the inner surface of the window glass, wherein:
- light emitted from the light emitting unit is reflected by the lightproof film and enters the light receiving unit; and
- the lightproof film has a temperature substantially same with that of the inner surface of the window glass.

9. The window fog detecting apparatus according to claim 8, wherein the glass temperature sensor is integrated with the lightproof film.

10. The window fog detecting apparatus according to claim 4, wherein the light emitting unit emits light pulses at a predetermined interval.

11. The window fog detecting apparatus according to claim 1, further comprising:
- an air temperature sensor for detecting a temperature of air at the interior side of the window glass; and
- a glass surface relative humidity calculating unit, wherein:
- the optical type fog detecting sensor includes:
  - an infrared light emitting unit which emits light pulses at a predetermined interval; and
  - an infrared light receiving unit,
  - wherein the fog occurrence at the window glass is detected based on a light receiving amount of the infrared light receiving unit when the infrared light emitting unit emits light, and a temperature of the window glass is detected based on the light receiving amount of the infrared light receiving unit when the infrared light emitting unit does not emit light;
- the sensor output correcting unit corrects the relative humidity detected by the humidity sensor when the fog occurrence at the window glass is detected based on the light receiving amount of the infrared light receiving unit; and
- the glass surface relative humidity calculating unit calculates a relative humidity of a surface of the interior side of the window glass based on an output value of the glass temperature detected by the infrared light receiving unit and output values of the humidity sensor and the air temperature sensor.

12. An air conditioner for a vehicle which has the window fog detecting apparatus according to claim 2, the air conditioner comprising:
- an inside/outside air switching unit for switching suction air between inside air and outside air by opening/closing an inside air introduction port and an outside air introduction port;
- a blowing unit which blows air having been introduced through at least one of the inside air introduction port and the outside air introduction port toward an interior of a passenger compartment of the vehicle;
- a cooling heat exchanger for cooling air blown by the blowing unit;
- a heating heat exchanger for heating air blown by the blowing unit;
- a case unit having a plurality of blowing-out ports, through which air having been temperature-conditioned by the cooling heat exchanger and the heating heat exchanger is blown toward the interior of the passenger compartment; and
- a plurality of blowing-out mode doors for switching a plurality of blowing-out modes by opening/closing the blowing-out ports, wherein:

the blowing-out ports include a defroster blowing-out port, through which air is blown toward a windshield of the vehicle;

the window fog detecting apparatus is mounted at a surface of the windshield, the surface being at an interior side of the passenger compartment; and at least one of an inside/outside air switching control via the inside/outside air switching unit, an air amount control via the blowing unit, and a blowing-out mode switching control via the blowing-out mode doors is performed based on a calculation value of the glass surface relative humidity calculating unit.

13. An air conditioner for a vehicle which has the window fog detecting apparatus according to claim 11, the air conditioner comprising:

an inside/outside air switching unit for switching suction air between inside air and outside air by opening/closing an inside air introduction port and an outside air introduction port;

a blowing unit which blows air having been introduced through at least one of the inside air introduction port and the outside air introduction port toward an interior of a passenger compartment of the vehicle;

a cooling heat exchanger for cooling air blown by the blowing unit;

a heating heat exchanger for heating air blown by the blowing unit;

a case unit having a plurality of blowing-out ports, through which air having been temperature-conditioned by the cooling heat exchanger and the heating heat exchanger is blown toward the interior of the passenger compartment; and a plurality of blowing-out mode doors for switching a plurality of blowing-out modes by opening/closing the blowing-out ports, wherein:

the blowing-out ports include a defroster blowing-out port, through which air is blown toward a windshield of the vehicle;

the window fog detecting apparatus is mounted at a surface of the windshield, the surface being at an interior side of the passenger compartment; and at least one of an inside/outside air switching control via the inside/outside air switching unit, an air amount control via the blowing unit, and a blowing-out mode switching control via the blowing-out mode doors is performed based on a calculation value of the glass surface relative humidity calculating unit.

14. The air conditioner according to claim 12, further comprising a compressor for circulating refrigerant through the cooling heat exchanger, wherein:

a target value of a cooling degree of the cooling heat exchanger is set so that the relative humidity of the inner surface of the window glass is within a predetermined range; and a capability of the compressor is controlled so that an actual cooling degree of the cooling heat exchanger becomes substantially equal to the target value.

15. The window fog detecting apparatus according to claim 3, wherein when a non-occurrence of fog at the window glass is indicated by the relative humidity detected by the humidity senor and a fog occurrence at the window glass is determined based on the output values of the optical fog detecting sensor, the sensor output correction unit corrects the calculation formula based on the output values of the optical fog detecting sensor so that the calculation value of the relative humidity calculating unit becomes substantially equal to a relative humidity at an interior air temperature at which the glass surface relative humidity is 100%, the interior air temperature being the temperature of air at the interior side of the window glass.

16. The window fog detecting apparatus according to claim 3, wherein in the case where the anti-fog control based on the relative humidity is not performed even when the relative humidity detected by the humidity senor indicates a fog occurrence at the window glass, the sensor output correction unit corrects the calculation formula based on the output values of the optical fog detecting sensor so that the calculation value of the relative humidity calculating unit becomes substantially equal to a relative humidity at the interior air temperature at which the glass surface relative humidity is 100%, when the fog occurrence at the window glass is determined based on the output values of the optical fog detecting sensor.

17. The window fog detecting apparatus according to claim 16, wherein:

the window glass is attached to a vehicle having an air conditioner; and in the case where the air conditioner is manually operated, the sensor output correction unit corrects the calculation formula based on the output values of the optical fog detecting sensor so that the calculation value of the relative humidity calculating unit becomes substantially equal to a relative humidity at the interior air temperature at which the glass surface relative humidity is 100%, when the fog occurrence at the window glass is determined based on the output values of the optical fog detecting sensor.

18. The window fog detecting apparatus according to claim 16, wherein:

the window glass is attached to a vehicle having an air conditioner, which is provided with a warming-up control at an air-conditioning start thereof so that conditioned air is not blown out until a cooling water temperature of an engine of the vehicle is higher than or equal to a predetermined value; and in the case where the warming-up control is performed, the sensor output correction unit corrects the calculation formula based on the output values of the optical fog detecting sensor so that the calculation value of the relative humidity calculating unit becomes substantially equal to a relative humidity at the interior air temperature at which the glass surface relative humidity is 100%, when the fog occurrence at the window glass is determined based on the output values of the optical fog detecting sensor.

* * * * *